(12) United States Patent
Gilbert et al.

(10) Patent No.: US 7,771,956 B2
(45) Date of Patent: Aug. 10, 2010

(54) METHOD FOR DETECTING THE PRESENCE OF A PHOSPHOLIPID

(75) Inventors: Gary E. Gilbert, Winchester, MA (US); Jialan Shi, Newton, MA (US); Christian W. Heegaard, Egaa (DK); Jan T. Rasmussen, Ry (DK)

(73) Assignees: Brigham & Women's Hospital, Inc., Boston, MA (US); United States of America Department of Veterans Affairs, Washington, DC (US)

( * ) Notice: Subject to any disclaimer, the term of this patent is extended or adjusted under 35 U.S.C. 154(b) by 753 days.

(21) Appl. No.: 10/562,269

(22) PCT Filed: Jun. 30, 2004

(86) PCT No.: PCT/US2004/017431
  § 371 (c)(1),
  (2), (4) Date: Feb. 12, 2007

(87) PCT Pub. No.: WO2005/005954
  PCT Pub. Date: Jan. 20, 2005

(65) Prior Publication Data
  US 2007/0249734 A1    Oct. 25, 2007

Related U.S. Application Data

(60) Provisional application No. 60/483,121, filed on Jun. 30, 2003.

(51) Int. Cl.
  *G01N 33/53* (2006.01)
(52) U.S. Cl. .......................... 435/7.2; 436/71
(58) Field of Classification Search .................. 435/7.2, 435/810, 975; 424/185.1, 45; 436/71
  See application file for complete search history.

(56) References Cited

U.S. PATENT DOCUMENTS

| | | | |
|---|---|---|---|
| 4,725,442 A | 2/1988 | Haynes | |
| 5,120,537 A | 6/1992 | Esmon et al. | |
| 5,258,497 A | 11/1993 | Reutelingsperger et al. | |
| 5,344,758 A | 9/1994 | Krilis et al. | |
| 5,455,031 A | 10/1995 | Ceriani et al. | |
| 5,505,955 A | 4/1996 | Peterson et al. | |
| 5,632,986 A | 5/1997 | Tait et al. | |
| 5,667,797 A | 9/1997 | Peterson et al. | |
| 5,783,662 A | 7/1998 | Janmey et al. | |
| 5,846,743 A | 12/1998 | Janmey et al. | |
| 5,849,600 A | 12/1998 | Nixon et al. | |
| 5,874,409 A | 2/1999 | Victoria et al. | |
| 5,955,437 A | 9/1999 | Reutelingsperger | |
| 5,972,337 A | 10/1999 | Ceriani et al. | |
| 6,194,214 B1 | 2/2001 | Kraus | |
| 6,284,475 B1 | 9/2001 | Rand | |
| 6,312,694 B1 | 11/2001 | Thorpe et al. | |
| 6,410,775 B1 | 6/2002 | Victoria et al. | |
| 7,354,897 B2 * | 4/2008 | Gilbert et al. | 514/2 |
| 2003/0022221 A1 | 1/2003 | Langit et al. | |
| 2004/0197314 A1 | 10/2004 | Delcayre et al. | |
| 2004/0241179 A1 | 12/2004 | Raposo et al. | |
| 2006/0257431 A1* | 11/2006 | Albert et al. | 424/277.1 |

FOREIGN PATENT DOCUMENTS

| | | |
|---|---|---|
| EP | 1004664 A1 | 5/2000 |
| WO | WO 03/103700 A1 | 12/1803 |
| WO | WO 00/30667 | 6/2000 |

OTHER PUBLICATIONS

Shi J. et al. Lactadherin Inhibits Enzyme Complexes of Blood Coagulation by Competing for Phospholipid Binding Sites. Hemostasis, Thrombosis, and Vascular Biology 101(7)2629-2636, Apr. 1, 2003.*
Hvarregaard J, Andersen MH, Berglund L, Rasmussen JT, Petersen TE. Characterization of glycoprotein PAS-6/7 from membranes of bovine milk fat globules. Eur. J. Biochem. 1996;240:628-636.
Stubbs J, Lekutis C, Singer K, Bui A, Yuzuki D, Srinivasan U, et al. cDNA cloning of a mouse mammary epithelial cell surface protein reveals the existence of epidemal growth factor-like domains linked to factor VIII-like sequences. Proc. Natl. Acad. Sci., USA 1990;87:8417-8421.
Couto JR, Taylor MR, Godwin SG, Ceriani RL, Peterson JA. Cloning and sequence analysis of human breast epithelial antigen BA46 reveals an RGD cell adhesion sequence presented on an epidermal growth factor-like domain. DNA Cell Biol. 1996;15(4):281-6.
Andersen MH, Berglund L, Rasmussen JT, Petersen TE. Bovine PAS-6/7 binds $a_v b_5$ integrin and anionic phospholipids through two domains. Biochemistry 1997;36:5441-5446.
Taylor MR, Couto JR, Scallan CD, Ceriani RL, Peterson JA. Lactadherin (formerly BA46), a membrane-associated glycoprotein expressed in human milk and breast carcinomas, promotes Arg-Gly-Asp (RGD)-dependent cell adhesion. DNA Cell Biol. 1997;16(7):861-9.
Andersen MH, Graversen H, Fedosov SN, Petersen TE, Rasmussen JT. Functional analyses of two cellular binding domains of bovine lactadherin. Biochemistry 2000;39(20):6200-6.
Butler JE, Pringnitz DJ, Martens CL, Crouch N. Bovine-associated mucoprotein: I. Distribution among adult and fetal bovine tissues and body fluids. Differentiation 1980;17(1):31-40.
Peterson JA, Couto JR, Taylor MR, Ceriani RL. Selection of tumor-specific epitopes on target antigens for radioimmunotherapy of breast cancer. Cancer Res. 1995;55(23 Suppl):5847s-5851s.
Haggqvist B, Naslund J, Sletten K, Westermark GT, Mucchiano G, Tjernberg LO, et al. Medin: an integral fragment of aortic smooth muscle cell-produced lactadherin forms the most common human amyloid. Proc. Natl. Acad. Sci. U. S. A. 1999;96(15):8669-74.
Ensslin M, Calvete JJ, Thole HH, Sierralta WD, Adermann K, Sanz L, et al. Identification by affinity chromatography of boar sperm membrane-associated proteins bound to immobilized porcine zona pellucida. Mapping of the phosphorylethanolamine-binding region of spermadhesin AWN. Biol. Chem. Hoppe. Seyler 1995;376(12):733-8.

(Continued)

*Primary Examiner*—Ralph Gitomer
(74) *Attorney, Agent, or Firm*—Dinesh Agarwal, P.C.

(57) ABSTRACT

A method, kit and probe for detecting the presence of a phospholipid, such as phosphatidylserine, in a biological material is provided. A binding agent including lactadherin, a fragment of lactadherin, a functional equivalent of lactadherin, or a functional equivalent of a fragment of lactadherin, is used to detect the presence of any phospholipid.

8 Claims, 38 Drawing Sheets

OTHER PUBLICATIONS

Hanayama R, Tanaka M, Miwa K, Shinohara A, Iwamatsu A, Nagata S. Identification of a factor that links apoptotic cells to phagocytes. Nature 2002,417(6885):182-7.

Shi J, Gilbert GE. Lactadherin inhibits enzyme complexes of blood coagulation by competing for phospholipid binding sites. Blood 2003;101(7):2628-36.

Arai M, Scandella D, Hoyer L. Molecular basis of factor VIII inhibition by human antibodies. Antibodies that bind to the factor VIII light chain prevent the interaction of factor VIII with phospholipid. J. Clin. Invest. 1989;83:1978-1984.

Foster PA, Fulcher CA, Houghten RA, Zimmerman TS. Synthetic factor VIII peptides with amino acid sequences contained within the C2 domain of factor VIII inhibit factor VIII binding to phosphatidylserine. Blood 1990;75:1999-2004.

Ortel T, Devore-Carter D, Quinn-Allen M, Kane W. Deletion analysis of recombinant human factor V: Evidence for a phosphatidylserine binding site in the second C-type domain. J. Biol. Chem. 1992;267:4189-4198.

Gilbert GE, Furie BC, Furie B. Binding of human factor VIII to phospholipid vesicles. J. Biol. Chem. 1990;265:815-822.

Gilbert GE, Drinkwater D, Barter S, Clouse SB. Specificity of phosphatidylserine-containing membrane binding sites for factor VIII: Studies with model membranes supported by glass microspheres (Lipospheres). J. Biol. Chem. 1992;267:15861-15868.

Gilbert GE, Drinkwater D. Specific membrane binding of factor VIII is mediated by O-phospho-L-serine, a moiety of phosphatidylserine. Biochemistry 1993;32:9577-9585.

Comfurius P, Smeets EF, Willems GM, Bevers EM, Zwaal RFA. Assembly of the prothrombinase complex on lipid vesicles depends on the stereochemical configuration of the polar headgroup of phosphatidylserine. Biochemistry 1994;33(34):10319-10324.

Bardelle C, Furie B, Furie BC, Gilbert GE. Kinetic Studies of Factor VIII Binding to Phospholipid Membranes Indicate a Complex Binding Process. J. Biol. Chem. 1993;268:8815-24.

Gilbert GE, Arena AA. Phosphatidylethanolamine induces high affinity binding sites for factor VIII on membranes containing phosphatidyl-L-serine. J. Biol. Chem. 1995;270:18500-18505.

Gilbert GE, Arena AA. Unsaturated phospholipid acyl chains are required to constitute membrane binding sites for factor VIII. Biochemistry 1998;37(39):13526-35.

Pratt KP, Shen BW, Takeshima K, Davie EW, Fujikawa K, Stoddard BL. Structure of the C2 domain of human factor VIII at 1.5 angstrom resolution. Nature. 1999;402(6760):439-442.

Macedo-Ribeiro S, Bode W, Huber R, Quinn-Allen MA, Kim SW, Ortel TL, et al. Crystal structures of the membrane-binding C2 domain of human coagulation factor V. Nature. 1999;402(6760):434-439.

Kim SW, Quinn-Allen MA, Camp JT, Macedo-Ribeiro S, Fuentes-Prior P, Bode W, et al. Identification of functionally important amino acid residues within the C2-domain of human factor V using alanine-scanning mutagenesis. Biochemistry 2000;39(8):1951-8.

Gilbert GE, Kaufman RJ, Arena AA, Miao H, Pipe SW. Four hydrophobic amino acids of the factor VIII C2 domain are constituents of both the membrane-binding and von Willebrand factor-binding motifs. J Biol Chem 2002;277(8):6374-81.

Peterson JA, Patton S, Hamosh M. Glycoproteins of the human milk fat globule in the protection of the breast-fed infant against infections. Biol. Neonate 1998;74(2):143-62.

Bevers E, Comfurius P, Zwaal R. Changes in membrane phospholipid distribution during platelet activation. Biochim. Biophys. Acta 1983;736:57-66.

Dachary-Prigent J, Freyssinet JM, Pasquet JM, Carron JC, Nurden AT. Annexin V as a probe of aminophospholipid exposure and platelet membrane vesiculation: a flow cytometry study showing a role for free sulfhydryl groups. Blood 1993;81(10):2554-65.

Alberio L, Safa O, Clemetson KJ, Esmon CT, Dale GL. Surface expression and functional characterization of alpha-granule factor V in human platelets: effects of ionophore A23187, thrombin, collagen, and convulxin. Blood 2000;95(5):1694-702.

Zwaal R, Comfurius P, van Deenen L. Membrane asymmetry and blood coagulation. Nature 1977;268:358-360.

Bevers E, Comfurius P, Van Rijn J, Hemker H, Zwaal R. Generation of Prothrombin-Converting Activity and the Exposure of Phosphatidylserine at the Outer Surface of Platelets. Eur. J. Biochem. 1982;122:429-436.

Seigneuret M, Devaux PF. ATP-dependent asymmetric distribution of spin-labeled phospholipids in the erythrocyte membrane: Relation to shape changes. Proc. Natl. Acad. Sci., USA 1984;81:3751-3755.

Tracy P, Peterson J, Nesheim M, McDuffie F, Mann K. Interaction of coagulation factor V and factor Va with platelets. J. Biol. Chem. 1979;254:10354-61.

Swords NA, Tracy PB, Mann KG. Intact Platelet Membranes, Not Platelet-Released Microvesicles, Support the Procoagulant Activity of Adherent Platelets. Arterioscler. Thromb. 1993;13(11):1613-1622.

Ahmad SS, Rawala-Sheikh R, Ashby B, Walsh PN. Platelet receptor-mediated factor X activation by factor IXa: High-affinity factor IXa receptors induced by factor VIII are deficient on platelets in Scott syndrome. J. Clin. Invest. 1989;84:824-828.

Gilbert GE, Sims PJ, Wiedmer T, Furie B, Furie BC, Shattil SJ. Platelet-derived microparticles express high affinity receptors for factor VIII. J. Biol. Chem. 1991;266:17261-68.

Comfurius P, Bevers EM, Zwaal RFA. Enzymatic synthesis of phosphatidylserine on small scale by use of a one-phase system. J. Lipid Res. 1990;31:1719-1721.

Hope MJ, Bally MB, Webb G, Cullis PR. Production of large unilamellar vesicles by a rapid extrusion procedure. Characterization of size distribution, trapped volume and ability to maintain a membrane potential. Biochim. Biophys. Acta 1985;812:55-65.

Chen P, Toribara T, Warner H. Microdetermination of phosphorus. Anal. Chem. 1956;28:1756-1758.

Huang C, Mason J. Geometric packing constraints in egg phosphatidylcholine vesicles. Proc. Natl. Acad. Sci., USA 1978;75:308-310.

Bangham AD, Standish MM, Watkins JC. Diffusion of univalent ions across the lamellae of swollen phospholipids. J. Mol. Biol. 1965;13:238-252.

Pusey M, Mayer L, Wei G, Bloomfield V, Nelsestuen G. Kinetic and Hydrodynamic Analysis of Blood Clotting Factor V-Membrane Binding. Biochemistry 1982;21:5262-5269.

Abbott A, Nelsestuen G. Association of a Protein with Membrane Vesicles at the Collisional Limit: Studies with Blood Coagulation Factor Va Light Chain Also Suggest Major Differences between Small and Large Unilamellar Vesicles. Biochemistry 1987;26:7994-8003.

Bloom JW. The interaction of rDNA factor VIII, factor VIIIdes-797-1562 and factor VIIIdes-797-1562 derived peptides with phospholipid. Throm. Res. 1987;48:439-448.

Epand RM, Stevenson C, Bruins R, Schram V, Glaser M. The chirality of phosphatidylserine and the activation of protein kinase C. Biochemistry 1998,37(35):12068-73.

Berden JA, Barker RW, Radda GK. NMR studies on phospholipid bilayers. Some factors affecting lipid distribution. Biochim. Biophys. Acta 1975;375(2):186-208.

Barsukov LI, Victorov AV, Vasilenko IA, Evstigneeva RP, Bergelson LD. Investigation of the inside-outside distribution, intermembrane exchange and transbilayer movement of phospholipids in sonicated vesicles by shift reagent NMR. Biochim. Biophys. Acta 1980;598(1):153-68.

Litman BJ. Determination of molecular asymmetry in the phosphatidylethanolamine surface distribution in mixed phospholipid vesicles. Biochemistry 1974;13(14):2844-8.

Koynova RD, Tenchov BG. Effect of ion concentration on phosphatidylethanolamine distribution in mixed vesicles. Biochim. Biophys. Acta 1983;727(2):351-6.

Lentz BR, Litman BJ. Effect of head group on phospholipid mixing in small, unilamellar vesicles: mixtures of dimyristoylphosphatidylcholine and dimyristoylphosphatidylethanolamine. Biochemistry 1978;17(25):5537-43.

Nordlund JR, Schmidt CF, Dicken SN, Thompson TE. Transbilayer distribution of phosphatidylethanolamine in large and small unilamellar vesicles. Biochemistry 1981;20(11):3237-41.

Tait JF, Gibson D. Phospholipid binding of annexin V: effects of calcium and membrane phosphatidylserine content. Arch. Biochem. Biophys. 1992;298(1):187-91.

Andree H, Reutelingsperger C, Hauptmann R, Hemker H, Hermens W, Willems G. Binding of vascular anticoagulant a (VACa) to planar phospholipid bilayers. J. Biol. Chem. 1990;265:4923-4928.

Andree HA, Stuart MC, Hermens WT, Reutelingsperger CP, Hemker HC, Frederik PM, et al. Clustering of lipid-bound annexin V may explain its anticoagulant effect. J. Biol. Chem. 1992;267(25):17907-12.

Swairjo MA, Concha NO, Kaetzel MA, Dedman JR, Seaton BA. Ca2+-bridging mechanism and phospholipid head group recognition in the membrane-binding protein annexin V. Nat. Struct. Biol. 1995;2:968-974.

Pigault C, Follenius-Wund A, Schmutz M, Freyssinet JM, Brisson A. Formation of two-dimensional arrays of annexin V on phosphatidylserine-containing liposomes. J. Mol. Biol. 1994;236(1):199-208.

Koopman G, Reutelingsperger CP, Kuijten GA, Keehnen RM, Pals ST, van Oers MH. Annexin V for flow cytometric detection of phosphatidylserine expression on B cells undergoing apoptosis. Blood 1994;84(5):1415-20.

Connor J, Bucana C, Fidler IJ, Schroit AJ. Differentiation-dependent expression of phosphatidylserine in mammalian plasma membranes: Quantitative assessment of outer-leaflet lipid by prothrombinase complex formation. Proc. Natl. Acad. Sci. USA 1989;86:3184-3188.

Poste G, Papahadjopoulos D. Lipid vesicles as carriers for introducing materials into cultured cells: influence of vesicle lipid composition on mechanism(s) of vesicle incorporation into cells. Proc. Natl. Acad. Sci. U. S. A. 1976;73(5):1603-7.

Batzri S, Korn ED. Interaction of phospholipid vesicles with cells. Endocytosis and fusion as alternate mechanisms for the uptake of lipid-soluble and water-soluble molecules. J. Cell Biol. 1975;66(3):621-34.

Chang CP, Zhao J, Wiedmer T, Sims PJ. Contribution of platelet microparticle formation and granule secretion to the transbilayer migration of phosphatidylserine. J. Biol. Chem. 1993;268:7171-7178.

McIntyre JC, Sleight RG. Fluorescence Assay for Phospholipid Membrane Assymetry. Biochemistry 1991;30:11819-11827.

Lawler J, Hynes RO. An integrin receptor on normal and thrombasthenic platelets that binds thrombospondin. Blood 1989;74(6):2022-7.

Bevers E, Wiedmer T, Comfurius P, Shattil S, Weiss H, Zwaal R, et al. Defective Ca2+-Induced Microvesiculation and Deficient Expression of Procoagulant Activity in Erythrocytes From a Patient With a Bleeding Disorder: A Study of the Red Blood Cells of Scott Syndrome. Blood 1992;79:380-388.

Jain MK, Rogers J, Marecek JF, Ramirez F, Eibl H. Effect of the structure of phospholipid on the kinetics of intravesicle scooting of phospholipase A2. Biochim. Biophys. Acta 1986;860(3):462-74.

Newburg DS, Peterson JA, Ruiz-Palacios GM, et al. Role of human-milk lactadherin in protection against symptomatic rotavirus infection. Lancet. 1998;351:1160-1164.

Tait JF, Gibson D,Fujikawa K. Phospholipid binding properties of human placental anticoagulant protein-1, a member of the lipocortin family. J Biol Chem. 1989;264:7944-7949.

Crompton MR, Moss SE,Crumpton MJ. Diversity in the lipocortin/calpactin family. Cell. 1988;55:1-3.

Tait JF, Sakata MS, McMullen BA, et al. Placental anticoagulant proteins: Isolation and comparative characterization of four members of the lipocortin family. Biochem. 1988;27:6268-6276.

Gilbert GE,Arena AA. Activation of the factor VIIIa-factor IXa enzyme complex of blood coagulation by membranes containing phosphatidyl-L-serine. J Biol Chem. 1996;271:11120-11125.

Johnson SM, Bangham AD, Hill MW,Korn ED. Single bilayer liposomes. Biochim Biophys Acta. 1971;233:820-826.

Neuenschwander PF,Morrissey JH. Deletion of the membrane anchoring region of tissue factor abolishes autoactivation of factor VII but not cofactor function. Analysis of a mutant with a selective deficiency in activity. J Biol Chem. 1992;267:14477-14482.

Lollar P,Fass DN. Inhibition of activated porcine factor IX by dansyl-glutamyl-glycylarginyl-chloromethylketone. Arch Biochem Biophys. 1984;233:438-446.

Govers-Riemslag JW, Janssen MP, Zwaal RF,Rosing J. Prothrombin activation on dioleoylphosphatidylcholine membranes. Eur J Biochem. 1994;220:131-138.

Ueno M, Tanford C,Reynolds JA. Phospholipid vesicle formation using nonionic detergents with low monomer solubility. Kinetic factors determine vesicle size and permeability. Biochem. 1984;23:3070-3076.

Mann KG, Nesheim ME, Church WR, Haley P,Krishnaswamy S. Surface-dependent reactions of the vitamin K-dependent enzyme complexes. Blood. 1990;76:1-16.

Freyssinet JM, Gauchy J,Cazenave JP. The effect of phospholipids on the activation of protein C by the human thrombin-thrombomodulin complex. Biochem J. 1986;238:151-157.

Suzuki K, Stenflo J, Dahlback B,Teodorsson B. Inactivation of human coagulation factor V by activated protein C. J Biol Chem. 1983;258:1914-1920.

Connor J,Schroit A. Transbilayer movement of phosphatidylserine in erythrocytes: Inhibition of transport and preferential labeling of a 31000-dalton protein by sulfhydryl reactive reagents. Biochem. 1988;27:848-851.

Connor J, Bucana C, Fidler IJ,Schroit AJ. Differentiation-dependent expression of phosphatidylserine in mammalian plasma membranes: Quantitative assessment of outer-leaflet lipid by prothrombinase complex formation. Proc Natl Acad Sci USA. 1989;86:3184-3188.

Fadok VA, Voelker DF, Campbell PA, et al. Exposure of phosphatidylserine on the surface of apoptotic lymphocytes triggers specific recognition and removal by macrophages. J Immunol. 1992;148:2207-2216.

van Heerde WL, Poort S, van 't Veer C, Reutelingsperger CP,de Groot PG. Binding of recombinant annexin V to endothelial cells: effect of annexin V binding on endothelial-cell-mediated thrombin formation. Biochem J. 1994;302 ( Pt 1):305-312.

London F, Ahmad SS,Walsh PN. Annexin V inhibition of factor IXa-catalyzed factor X activation on human platelets and on negatively-charged phospholipid vesicles. Biochem. 1996;35:16886-16897.

Nimpf J, Bevers EM, Bomans PH, et al. Prothrombinase activity of human platelets is inhibited by beta 2-glycoprotein-I. Biochim Biophys Acta. 1986;884:142-149.

Mori T, Takeya H, Nishioka J, Gabazza EC,Suzuki K. beta 2-Glycoprotein I modulates the anticoagulant activity of activated protein C on the phospholipid surface. Thromb Haemost. 1996;75:49-55.

McNeil HP, Simpson RJ, Chesterman CN,Krilis SA. Anti-phospholipid antibodies are directed against a complex antigen that includes a lipid-binding inhibitor of coagulation: beta 2-glycoprotein I (apolipoprotein H). Proc Natl Acad Sci U S A. 1990;87:4120-4124.

Takeya H, Mori T, Gabazza EC, et al. Anti-beta2-glycoprotein I (beta2GPI) monoclonal antibodies with lupus anticoagulant-like activity enhance the beta2GPI binding to phospholipids. J Clin Invest. 1997;99:2260-2268.

Bancsi LF, van der Linden IK,Bertina RM. Beta 2-glycoprotein I deficiency and the risk of thrombosis. Thromb Haemost. 1992;67:649-653.

Ceriani RL, Sasaki M, Sussman H, Wara WM,Blank EW. Circulating human mammary epithelial antigens in breast cancer. Proc Natl Acad Sci U S A. 1982;79:5420-5424.

Enoch HG, Strittmatter P. Formation of properties of 1000-Å-diameter, single-bilayer phospholipid vesicles. Proceeding of the National Academy of Scienes, USA 1979;76:145-149.

Larocca et al. *A Mr 46,000 human milk fat globule protein that is highly expressed in human breast tumors contains factor VIII-like domains.* Cancer Res. Sep. 15, 1991, vol. 51, No. 18, pp. 4994-4998.

Ortel et al. *Characterization of an acquired inhibitor to coagulation factor V. Antibody binding to the second C-type domain of factor V inhibits the binding of factor V to phosphatidylserine and neutralizes procoagulant activity.* J. Clin. Invest. Dec. 1992, vol. 90, pp. 2340-2347.

Aoki et al., "Stage specific expression of milk fat globule membrane glycoproeins in mouse mammary gland: comparison of MFG-E8, butyrophilin, and CD36 with a major mile protein, bet caselin", Biochemicica et Biophysica Acta 1334: 182-190 (1997).

Kim D.H, Azuma N, Tanaka H, Kanno C. Structures of the N-linked sugar chains in the PAS-6 glycoprotein from the bovine milk globule memberane. Glycoconjugate Journal (1998) 15: 361-369.

Shi J., Heegaard C.W., Rasnussen J.T., Gilbert G.E. Lactadherin binds selectively to membranes containing phosphatidyl-L-serine and increased curvature. Biochimica et Biophysica Acta 1667 (2004) 82-90.

Shi J, Gilbert GE. Lactadherin inhibits enzyme complexes of blood coagulation by competing for phospholipid binding sites. Blood Dec. 2002;100(11):262a, American Society of Hematology Abstract (1 page).

* cited by examiner

METHOD FOR DETECTING THE PRESENCE OF A PHOSPHOLIPID

CROSS-REFERENCE TO RELATED APPLICATIONS

The present application claims priority on prior U.S. Provisional Application Ser. No. 60/483,121, filed Jun. 30, 2003, and which is incorporated herein in its entirety by reference.

STATEMENT REGARDING FEDERALLY SPONSORED RESEARCH OR DEVELOPMENT

The work leading to the present invention was supported by one or more grants from the U.S. Government, including National Heart, Lung, and Blood Institute Grant R01 HL57867. The U.S. Government therefore has certain rights in the invention.

BACKGROUND OF THE INVENTION

The present invention is generally directed to detecting phospholipids, and more particularly to using lactadherin or a fragment thereof as an agent for detecting the presence of a phospholipid, such as phosphatidylserine (PS), on a cell membrane.

Lactadherin is a MW 47,000 glycoprotein of milk fat globules. It has also been known as PAS-6/7, indicating the two glycosylation variants (Reference 1), bovine-associated mucoprotein, BA-46, P47, and MFG-E8 (Reference 2). Lactadherin has a domain structure of EGF1-EGF2-C1-C2 in which EGF indicates epidermal growth factor homology domains, and the C domains share homology with the discoidin family including the lipid-binding "C" domains of blood coagulation factor VIII and factor V (Reference 2). The second EGF domain displays an Arg-Gly-Asp motif (Reference 3) which binds to the $\alpha_v\beta_5$ and $\alpha_v\beta_3$ integrins (References 1 and 4-6). The second C domain binds to phospholipids (Reference 6).

In milk fat globules, lactadherin lines the surface of the phospholipid bilayer which surrounds the central triglyceride droplet, apparently stabilizing the bilayer (Reference 7). In tissue sections lactadherin is found within the milk ductules and localized on the apical portion of secretory epithelium in the breast (Reference 7). Abundant expression by breast carcinoma makes lactadherin a potential target for antigen-guided radiation therapy (Reference 8). Lactadherin also lines the apical surface of epithelia in the biliary tree, the pancreas, and sweat glands (Reference 7) and is synthesized by aortic medial smooth muscle cells (Reference 9). Lactadherin has been identified as a zona pellucida-binding protein on the acrosomal cap of sperm (Reference 10). Function in these tissues remains unknown. Stimulated macrophages, but not quiescent macrophages, synthesize and secrete lactadherin in vitro (Reference 11). Lactadherin then binds to apoptotic cells expressing phosphatidylserine and mediates phagocytosis of the dying cells via interaction of the lactadherin EGF domain with macrophage integrin(s).

We have recently found that, in vitro, lactadherin functions as a potent anticoagulant (Reference 12). Homology between the lactadherin and factor VIII C domains correlates with efficient competition for membrane binding sites recognized by both factor VIII and factor V. Lactadherin inhibits the factor Xase complex, in which factor VIII functions, and the prothrombinase complex, in which factor V functions. Lactadherin also inhibited the factor VIIa-tissue factor complex and competed with vitamin K dependent factor IXa for membrane binding sites indicating a capacity to block binding sites for non-homologous coagulation proteins. The inhibitory properties of lactadherin contrasted with those of annexin V. Although annexin V binds to phosphatidylserine-containing membranes with high affinity, it functions well as an anticoagulant only when the phosphatidylserine content exceeds 4% and the membrane curvature is very limited. By contrast, lactadherin was an efficient anticoagulant on membranes with <4% phosphatidylserine and regardless of curvature. The in vitro anticoagulant properties of lactadherin suggest the possibility that it may have an anticoagulant function during some physiologic or pathologic conditions (Reference 12).

Blood coagulation factor VIII and factor V bind to phospholipid membranes via "C" domains which share homology with lactadherin "C" domains (References 13-15). Remarkable features of membrane binding include high affinity ($K_D$ approx. 2 nM) (Reference 16) and sufficient specificity so that no plasma proteins compete for membrane binding sites (Reference 17). Factor VIII binds via stereo-selective interaction with the phospho-L-serine motif of phosphatidylserine (Ptd-L-Ser) (Reference 18). Factor V also exhibits stereoselective interaction with Ptd-L-Ser (Reference 19). Both proteins associate rapidly with membrane binding sites but have increased affinity conferred by a second, slower binding interaction (Reference 20). Binding of factor VIII is enhanced by the presence of phosphatidylethanolamine (PE) in the membrane (Reference 21), by unsaturated phospholipid acyl chains (Reference 22), and by membrane curvature (Reference 21). The crystal structures of the C2 domains of factors VIII and V suggest that membrane binding is mediated by two pairs of hydrophobic residues displayed at the tips of β-hairpin turns (References 23 and 24). Mutagenesis studies have confirmed the role of these residues in phospholipid binding (References 25 and 26). The homology of the lactadherin C domains with those of factors VIII and V suggests that similar phospholipid binding properties may be mediated by hydrophobic residues on putative β-hairpin turns. Indeed, lactadherin has been found to bind Ptd-L-Ser adsorbed to plastic (Reference 27) and to utilize primarily the C2 domain in its lipid binding (Reference 6). Furthermore, the capacity of lactadherin to quantitatively compete with both factor VIII and factor V for membrane binding sites (Reference 12) suggests that it has high affinity for these membranes and a similar mechanism of binding.

The discovery that lactadherin functions as a anticoagulant was the subject of U.S. Provisional Application Ser. No. 60/386,562, filed Jun. 7, 2002, and International Application No. PCT/US03/15404, filed Jun. 6, 2003, both incorporated herein in their entirety by reference.

OBJECTS AND SUMMARY OF THE INVENTION

The principal object of the present invention is to provide an agent which can be used to detect the presence of a phospholipid, such as phosphatidylserine, in a biological material. The agent includes lactadherin, a fragment of lactadherin, a functional equivalent of lactadherin, or a functional equivalent of a fragment of lactadherin.

An object of the present invention is to provide an agent which binds to phosphatidylserine containing membranes.

Another object of the present invention is to provide an agent which has a stereoselective preference for binding to phosphatidylserine and preference for binding to highly or sharply curved membranes.

Yet another object of the present invention is to provide an agent which exhibits specificity for phospho-L-serine moiety of phosphatidylserine and high affinity for membrane binding sites similar to blood clotting factors VIII and V.

Still yet another object of the present invention is to provide an agent which binds to phosphatidylserine containing membranes independently of $Ca^{++}$ and/or phosphatidylethanolamine (PE).

An additional object of the present invention is to provide an agent which exhibits a steep positive relationship between phosphatidylserine content and number of binding sites over a range of 0-2% of phosphatidylserine.

Lactadherin, a milk protein, contains discoidin-type lectin domains with homology to the phosphatidylserine-binding domains of blood coagulation factor VIII and factor V. Previously, we found that lactadherin functions, in vitro, as a potent anticoagulant by competing with blood coagulation proteins for phospholipid binding sites (Reference 12). In the present invention, we determine the membrane-binding properties that correlate to the anticoagulant capacity. We labeled bovine lactadherin with fluorescein and evaluated binding to membranes of composition phosphatidylserine (Ptd-L-Ser): phosphatidylethanolamine:phosphatidylcholine, 4:20:76 supported by 2 μm diameter glass microspheres. Lactadherin bound saturably with an apparent $K_D$ of 3.3±0.4 nM in a $Ca^{++}$-independent manner. The number of lactadherin binding sites increased proportionally to the Ptd-L-Ser content over a range 0-2% Ptd-L-Ser and less rapidly for higher Ptd-L-Ser content. Inclusion of phosphatidylethanolamine in phospholipid vesicles did not enhance the apparent affinity or number of lactadherin binding sites. The number of sites was at least 4-fold higher on sonicated vesicles than on extruded vesicles of 0.1 μm diameter, indicating that lactadherin binding is enhanced by membrane curvature. Lactadherin bound to membranes with synthetic dioleoyl Ptd-L-Ser, but not dioleoyl Ptd-D-Ser indicating stereoselective recognition of Ptd-L-Ser. Factor VIII and factor V each competed for 40-70% of the phospholipid binding sites that bound lactadherin, but not the residual 30-60%. We conclude that lactadherin resembles factor VIII and V with stereoselective preference for Ptd-L-Ser and preference for highly curved membranes. Lactadherin differs from these proteins in recognizing a wider range of phospholipid binding sites.

At least one of the above-noted objects is met, in part, by the present invention, which in one aspect includes detecting the presence of a phospholipid in a biological material by subjecting a biological material to a binding agent including lactadherin, a fragment of lactadherin, a functional equivalent of lactadherin, or a functional equivalent of a fragment of lactadherin, allowing binding between any phospholipid present and the binding agent, and detecting the presence of any phospholipid bound to the binding agent.

Another aspect of the invention includes blocking or reducing binding of a protein to a binding site by subjecting a binding site to a binding agent including lactadherin, a fragment of lactadherin, a functional equivalent of lactadherin, or a functional equivalent of a fragment of lactadherin.

Another aspect of the invention includes detecting phosphatidylserine-expressing cells by subjecting a biological material including, or suspect of including, phosphatidylserine-expressing cells, to a binding agent including lactadherin, a fragment of lactadherin, a functional equivalent of lactadherin, or a functional equivalent of a fragment of lactadherin, allowing binding between any cells present and the binding agent, and detecting the presence of any phosphatidylserine-expressing cells bound to the binding agent. An example of a cell type for which lactadherin can detect phosphatidylserine exposure is blood platelets. Blood platelets circulate with no phosphatidyslserine expressed on the outer membrane. However, platelets respond to some agonists by translocating phosphatidylserine (PS) from the inner leaflet of the plasma membrane to the outer leaflet (References 28-30). Exposed PS supports assembly and function of the prothrombinase and factor Xase complexes on the platelet membrane (References 31 and 32). Unstimulated platelets sequester PS on the inner leaflet of the plasma membrane with an ATP-dependent pump, correlating to absence of prothrombinase or factor Xase supporting activity (Reference 33). Thrombin is a strong platelet agonist, yet its capacity to stimulate platelet PS exposure is uncertain (References 29 and 30). Thrombin-stimulated platelets support function of the prothrombinase and factor Xase complexes, suggesting that PS is exposed (References 34-36). However, the failure of thrombin-stimulated platelets to provide binding sites for annexin V has raised doubt as to whether the prothrombinase and factor Xase activity is a consequence of PS exposure (Reference 29). Lactadherin can be used to detect PS exposure when the quantity of PS exposed is sufficient to support blood coagulation but insufficient to support binding of annexin V.

Another aspect of the invention includes protecting a biological material from the action of an enzyme by subjecting a biological material to be protected from an enzyme to a binding agent including lactadherin, a fragment of lactadherin, a functional equivalent of lactadherin, or a functional equivalent of a fragment of lactadherin, and allowing binding between the biological material and the binding agent to protect the biological material from the enzyme.

Another aspect of the invention is to provide a pharmacological bridge ligand, which includes lactadherin, a fragment of lactadherin, a functional equivalent of lactadherin, or a functional equivalent of a fragment of lactadherin. The ligand would provide a bridge between phosphatidylserine on a membrane surface and an Integrin on a cell. For example, lactadherin can be administered orally or intravenously as a complex with phospholipid vesicles containing a pharmaceutical agent or nutrient. Lactadherin would lead to selective binding and/or engulfment of the phospholipid vesicles by cells which contain lactadherin-binding integrins on their outer membrane.

Another aspect of the invention is to provide a composition for detecting the presence of a phospholipid in a biological material, which includes a binding agent including lactadherin, a fragment of lactadherin, a functional equivalent of lactadherin, or a functional equivalent of a fragment of lactadherin, and a suitable carrier.

Another aspect of the invention is to provide a kit for detecting the presence of a phospholipid in a biological material, which includes a binding agent including lactadherin, a fragment of lactadherin, a functional equivalent of lactadherin, or a functional equivalent of a fragment of lactadherin, and instructions for use of the binding agent.

Another aspect of the invention includes blocking or reducing the procoagulant activity of a cell by subjecting a cell to an agent including lactadherin, a fragment of lactadherin, a functional equivalent of lactadherin, or a functional equivalent of a fragment of lactadherin.

Another aspect of the invention is to provide a probe for detecting the presence of a phospholipid in a biological material, which includes a binding agent including lactadherin, a fragment of lactadherin, a functional equivalent of lactadherin, or a functional equivalent of a fragment of lactadherin.

BRIEF DESCRIPTION OF THE DRAWINGS

One of the above and other objects, novel features and advantages of the present invention will become apparent from the following detailed description of the invention, as illustrated in the drawings, in which:

FIG. 1B—The specificity of phospholipid binding sites for fluorescein-labeled lactadherin binding was evaluated in a competition experiment in which varying concentrations of lactadherin were mixed with 1 nM fluorescein-lactadherin prior to the addition of lipospheres;

FIG. 4A—Competition binding experiments like those described in the legend to FIG. 4 were performed with extruded vesicles of varying PE content. FIG. 4B—Competition binding experiments were performed with vesicles lacking Ptd-L-Ser and containing phosphatidylinositol or no negatively charged lipid. FIG. 4C—Binding to liposheres was evaluated in the presence of 1.5 mM $Ca^{++}$ or 1.5 mM EDTA with no $Ca^{++}$;

FIG. 5A—Binding of lactadherin to liposheres displaying 2% synthetic dioleoyl Ptd-L-Ser (●) vs. 2% synthetic Ptd-D-Ser (σ) vs. no phosphatidylserine (X) was evaluated by flow cytometry. FIG. 5B—The affinity of lactadherin for the isolated had group of Ptd-L-Ser or Ptd-D-ser was estimated in competition binding experiments with phospho-L-serine (⊕) vs. phospho-D-serine (σ) vs. phosphate (X). Phospho-L-serine inhibited binding with a $K_I$ of 160 mM (smooth line) whereas neither phospho-D-serine or phosphate inhibited binding more than 25% at concentrations as high as 0.35 M;

FIG. 7B—Four nM fluorescein-labeled lactadherin or annexin V was incubated with liposheres of various membrane compositions. FIG. 7C—Limited competition by annexin V for lactadherin binding sites. FIG. 7D—Limited competition by lactadherin for annexin V binding sites;

FIG. 8A—Unstimulated platelets. FIG. 8B—Platelets stimulated with 0.25 μM A23817 show increased binding of lactadherin, not annexin V. FIG. 8C—Platelets stimulated with 1.0 μM A23187 show some cells stained with either lactadherin only and others stained with both lactadherin and annexin V;

FIGS. 9A, B—Blockade of integrin function with echistatin and EDTA does not affect lactadherin binding. FIGS. 8C, D—Competition of PS-containing vesicles for lactadherin binding sites on platelets. FIGS. 8E, F—Inhibition of lactadherin binding to platelets by antibodies against the C2 domain.

FIG. 4A—Platelets were stimulated by 10 μM A23187 and thrombin production was measured. FIG. 4B—Platelets were stimulated by 0.5 μM A23187 and thrombin production was measured. FIG. 4C—Platelets were stimulated by 10 μM A23187 and factor Xa production was measured. FIG. 4D—Platelets were stimulated by 0.5 μM A23187 and factor Xa production was measured;

FIG. 12A—Binding of various concentrations of fluorescence-labeled lactadherin to platelets stimulated by 10 μM TRAP was measured by flow cytometry. FIG. 12B—Addition of more rapid exposure of fluorescence-labeled PS over the first two minutes following addition of TRAP. inset Platelets stimulated with A23187 exposed membrane PS and lost >90% NBD fluorescence over 8 minutes FIG. 12C—Reversibility of lactaderin binding site expression is after TRAP stimulation;

DETAILED DESCRIPTION OF THE INVENTION

Figure 1A:
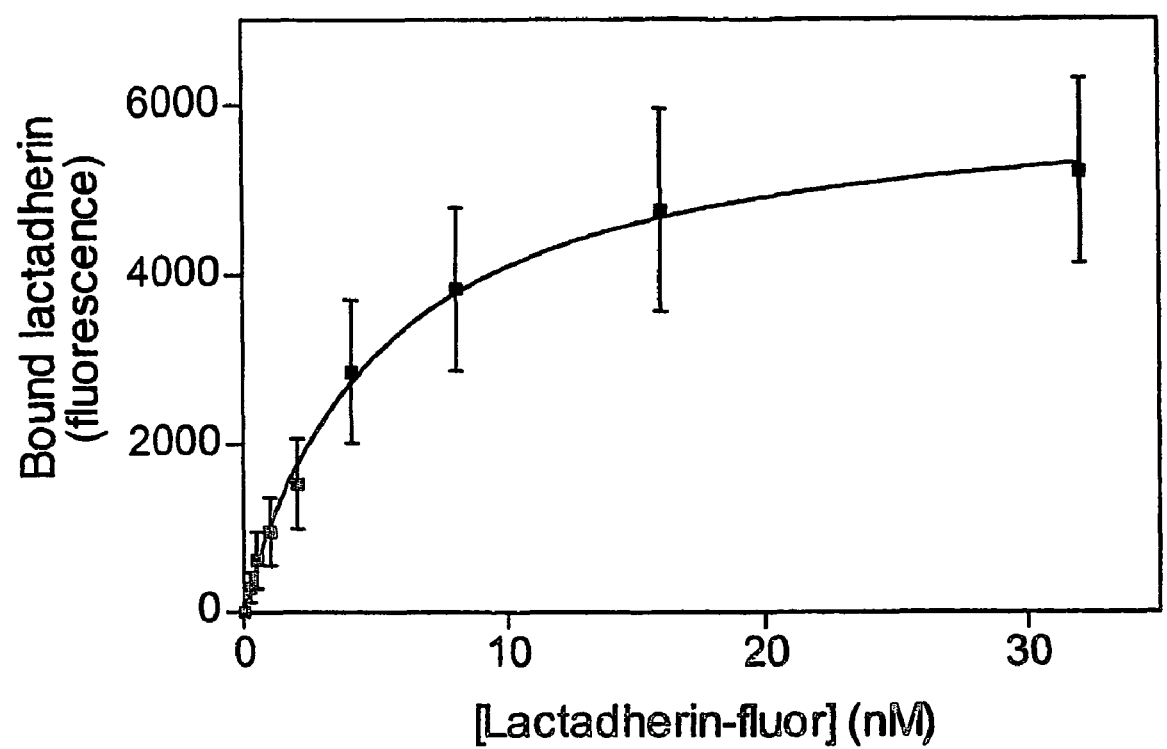
FIGS. 1A-B illustrate the binding of lactadherin to lipospheres.

The present invention is directed to characterizing the membrane-binding properties of lactadherin in the context of the properties of factor VIII and factor V, and is based, at least in part, on the discovery that lactadherin resembles factor VIII and factor V in a high affinity, stereo-selective recognition of Ptd-L-Ser and in preferential binding to highly curved membranes. Lactadherin differs from factor VIII in requiring fewer Ptd-L-Ser molecules per binding site and apparent indifference to PE.

Materials

Human factor V was obtained from Haematologic Technologies Inc. (Burlington, Vt.). Recombinant human factor VIII was a gift from D. Pittman of Genetics Institute, Cambridge, Mass. Bovine brain phosphatidylserine (Ptd-L-Ser), egg yolk phosphatidylethanolamine (PE), bovine liver phosphatidylinositol, egg sphingomyelin, egg phosphatidylcholine (PC) and dioleoyl PC were obtained from Avanti Polar Lipids (Alabaster, AL). Phospholipase D from *streptomyces*, phospho-L-serine phospho-D-serine, L-serine and D-serine were obtained from Sigma.

Purification and Fluorescein Labeling of Proteins

Lactadherin was purified from bovine milk as previously described (Reference 1). Lactadherin, 0.2 mg in 0.2 ml phosphate-buffered saline, was concentrated 10-fold by ultrafiltration with a Centricon YM-10 (Millipore, Bedford, Mass.) followed by dilution to the starting concentration into 0.1 M sodium carbonate buffer, pH 9.0. Fluorescein isothiocyanate (Molecular Probes, Eugene, Oreg.) 6 µl of 10 mg/ml solution in DMSO, was added to lactadherin and the mixture was incubated for one hour at RT in the dark. Free fluorescein was removed by gel filtration using a micro spin column equilibrated with 0.1 M sodium carbonate, 0.1 M betaine, 0.004% Tween-80, pH 9.0 (FluoReporter FITC Protein Labeling Kit, Molecular Probes, Eugene, Oreg.). Fluorescein-labeled lactadherin was concentrated approx. 10-fold by ultrafiltration using a Centricon YM-10, and diluted to approximately the original concentration in 0.15 M NaCl, 50 mM Tris-HCl, pH 7.5. Labeling efficiency was judged by comparison of absorbance at 490 nm to absorbance at 280 nm (correcting for fluorescein absorbance at 280 nm).

Factor VIII and factor V were labeled with fluorescein maleimide (Molecular Probes, Eugene, Oreg.) as previously described (References 17 and 37). Protein concentration of factor VIII was determined using a Micro-BCA Assay (Pierce, Rockford, Ill.) using bovine albumin as a standard.

Synthesis of Ptd-L-Ser and Ptd-D-Ser

Ptd-L-ser and Ptd-D-ser were synthesized by enzymatic transphosphatidylation of dioleoyl PC by phospholipase D and purified as previously described (Reference 38). Briefly, 50 mg of dioleoyl PC was suspended in 2 ml of 50% w/v L-serine or D-serine, 5% w/v octyl glucoside, 0.1 M $CaCl_2$, and 0.1 M Na Acetate and stirred for 3 hr at 45° C. The reaction was stopped by addition of EDTA and phospholipids were extracted with a 20:1 ratio of chloroform:methanol 1:1. Ptd-L-ser or Ptd-D-ser was purified from phosphatidic acid and residual PC by carboxymethylcellulose column chromatography (Reference 38). Fractions containing Ptd-L-ser or Ptd-D-ser were identified and analyzed for purity by thin layer chromatography on silica plates in a solvent system of chloroform:methanol:acetic acid:water 25:15:4:2. Phospholipids were visualized by spraying the plate with a 1:1 solution of molybdenum blue (Sigma, St Louis, Mo.) with 4.2 M sulfuric acid.

Preparation of Phospholipid Vesicles

Phospholipid vesicles were prepared by evaporating chloroform from the desired phospholipids, resuspending in methylene chloride and re-evaporating twice under argon. Large multilamellar vesicles were prepared by gently swirling tris-buffered saline (50 mM Tris, 150 mM NaCl, pH 7.4) over the dried lipid suspension until all lipid was suspended. Some of the large multilamellar vesicles were then utilized to prepare small unilamellar vesicles by sonication in a high intensity bath sonicator (Laboratory Supplies, Inc. Hicksville, N.Y.) under argon until visually clear (approx. 20 min.). Large unilamellar vesicles were made by extruding large multilamellar vesicle suspensions 20 times through two 2 stacked polycarbonate membranes (Millipore, Bedford, Mass.) in a High Pressure Extrusion Device (Sciema Technical Services, Vancouver, BC, Canada) under argon as described previously (Reference 39). Phospholipid concentration was determined by phosphorus assay (Reference 40). Vesicles were used fresh, or 1 ml aliquots were quick-frozen in liquid nitrogen, stored at −80° C., and thawed at 37° C. Storage at 4° C. before usage did not exceed 24 hours.

Flow Cytometry Phospholipid Binding Assay

Glass microspheres of 1.6 µm nominal diameter (Duke Scientific, Palo Alto, Calif.) were cleaned, size-restricted and covered with a phospholipid bilayer as previously described (Reference 17). Membranes supported by glass microspheres were washed three times in 0.15 M NaCl, 0.02 M Tris-HCl, 0.1% defatted bovine albumin, 10 µM egg PC as sonicated vesicles; stored at 4° C.; and used within 8 hours of synthesis. Fluorescein-labeled factor VIII (4 nM) was incubated with lactadherin or annexin V for 15 min at room temperature, the mixture was added to lipospheres for an additional 10 minutes, and membrane-bound fVIII was measured by flow cytometry. This procedure was performed on 150 µl aliquots with an approximate liposphere concentration of $1 \times 10^6$/ml using a Becton Dickinson FACSCalibur flow cytometer. Data acquisition was triggered by forward light scatter with all photomultipliers in the log mode. Noise was reduced during analysis by eliminating events with forward and side scatter values different from those characteristic of the lipospheres. Mean log fluorescence was converted to linear fluorescence for values depicted in the figures. Only experiments in which the fluorescence histogram indicated a log normal distribution, as judged by inspection, were analyzed quantitatively. Flow cytometry experiments were performed in 0.14 M NaCl, 0.02 M Trizma-HCl, 0.1% bovine albumin, pH 7.5 with $CaCl_2$ as specified for individual experiments.

Fluorescein-labeled lactadherin was incubated with $10^6$ lipospheres/ml in Tris-buffered saline, 1.5 mM $CaCl_2$, 0.1% BSA for 10 min. prior to evaluation of bound lactadherin by flow cytometry. The final concentrations of lactadherin were varied to estimate the affinity and stoichiometry of bound lactadherin.

Data Analysis

The equilibrium binding of lactadherin to lipospheres was fitted by non-linear, least squares data analysis using the standard binding model (assuming a single class of binding sites and that the fraction of bound lactadherin was small at each concentration evaluated). For experiments depicted in FIGS. 4A-C and 5A-B, data were normalized, then subtracted from 1 (to prepare curves representing the increasing fraction of bound lactadherin as a function of phospholipid concentration). This treatment is justified by assuming that the liposphere-bound lactadherin is proportional to the free lactadherin concentration over a range of 0-1 nM (see FIGS. 1A-B). The derived phospholipid binding curves were fitted to the equation: $Lacterin_{Bound}/Lacterin_{Total} = (Phospholipid/n)/(K_D + Phospholipid/n)$, rearranged as $$= Phospholipid/((K_D \times n) + Phospholipid)$$

using the Prism 3.0 software package. "Phospholipid" represents the total phospholipid concentration, "n" is the ratio of phospholipid monomers per binding site, and $K_D$ is the dissociation constant between a binding site and lactadherin. Curves were fitted for the composite variable, $K_D \times n$ because the data did not allow determination of both variables for all conditions.

Results

We hypothesized that lactadherin would exhibit membrane binding properties that resemble those of factor VIII, e.g. recognition of specific phospholipid binding sites and stereoselective interaction with Ptd-L-Ser. To test this hypothesis we prepared lactadherin labeled with fluorescein isothiocyanate as described above. The molar ratio of fluorescein to lactadherin was 1.2 in the first labeling and 1.3 in the $2^{nd}$ labeling.

Figure 1B:
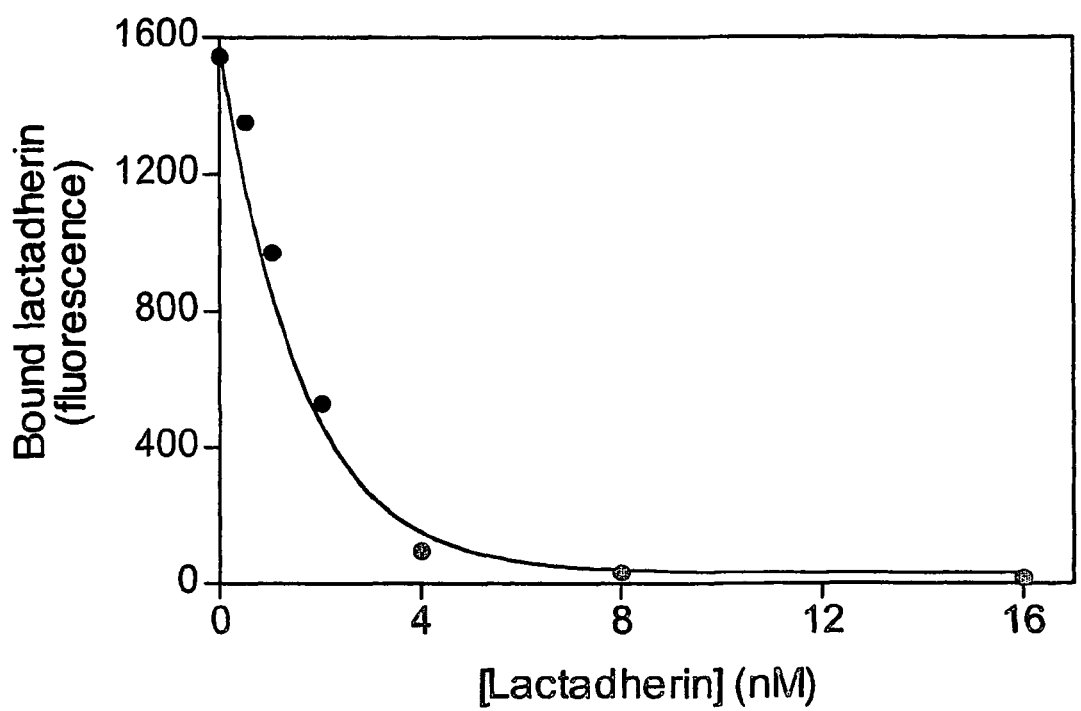

Fluorescein-labeled lactadherin interacted with phospholipid bilayers supported by glass microspheres (liposheres). The phospholipid composition was 4% Ptd-L-Ser, 20% PE, with the balance as PC. After 10 minutes, we measured bound lactadherin using flow cytometry (FIG. 1A). Lactadherin bound saturably to liposheres with half-maximal binding at a lactadherin concentration of approximately 3 nM. We fitted binding data with the standard binding model, which assumes equilibrium between a ligand and a single class of binding sites (smooth line). The best fit indicated a $K_D$ of 3.3±0.4 nM. Displayed data are mean±SD for 3 experiments with different batches of liposheres.

Non-labeled lactadherin competed with fluorescein-labeled lactadherin (FIG. 1B) for membrane binding sites. These data indicate that lactadherin binds to Ptd-L-Ser containing membranes with high affinity and that binding is not substantially altered by labeling lactadherin with fluorescein isothiocyanate.

Figure 2:
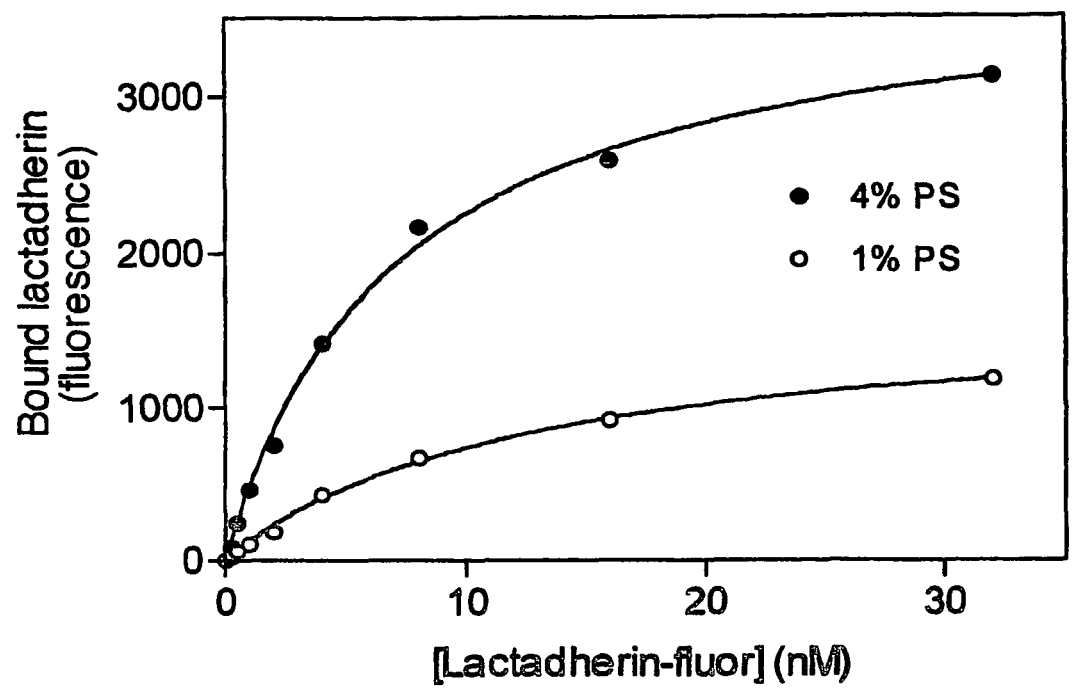
FIG. 2 illustrates the relationship between Ptd-L-Ser content and number of lactadherin binding sites.

In order to evaluate the relationship between membrane Ptd-L-Ser content and the binding of lactadherin, we evaluated binding of fluorescein-labeled lactadherin to membranes containing 1% Ptd-L-Ser (µ) vs. 4% Ptd-L-Ser (●) (FIG. 2). We observed saturable binding of lactadherin to both membrane types. The apparent $K_D$ for membranes of 1% Ptd-L-Ser was within 2-fold of membranes with 4% Ptd-L-Ser, while the fluorescence plateau of membranes with 4% Ptd-L-Ser was 2.3-fold higher than for membranes with 1% Ptd-L-Ser. This indicates that the major effect of increased Ptd-L-Ser content is to increase the number of Ptd-L-Ser binding sites rather than the affinity of lactadherin for membranes.

Figure 3A:
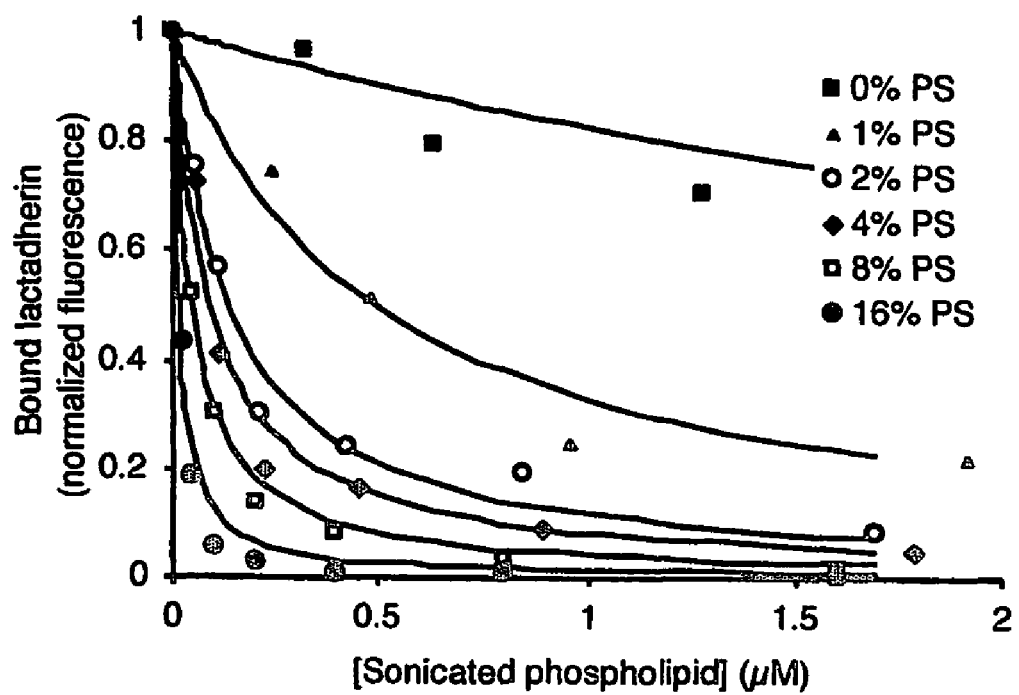
FIGS. 3A-D illustrate the relationship of membrane curvature and Ptd-L-Ser content to binding of lactadherin. Sonicated vesicles (FIG. 3A), extruded vesicles-0.1 μm diameter (FIG. 3B), and LMV (FIG. 3C) with the indicated Ptd-L-Ser content FIG. 3D. The reduction in free lactadherin with increasing vesicle concentrations was utilized to fit vesicle-binding curves according to the formula described under "Experimental procedures," (smooth lines)

To explore the effect of membrane curvature on formation of binding sites for lactadherin we performed competition binding experiments (FIGS. 3A-D). Phospholipid vesicles of varying diameter, and corresponding variation in membrane curvature, competed with liposheres for binding of 1 nM fluorescein-labeled lactadherin. Small unilamellar vesicles, prepared by sonication (nominal diameter of 20 nm (Reference 41)), exhibited the highest number of binding sites for lactadherin (FIG. 3A). Only 20% of lactadherin remained free to bind liposheres when vesicles of 16% Ptd-L-Ser were at a phospholipid concentration of 0.05 µM. The number of phospholipid monomers/binding site is <60 under these conditions because the number of binding sites must exceed the bound lactadherin concentration of 0.8 nM. This relationship places limits on the apparent dissociation constant and binding site size for the phospholipid vesicles. Because n<60 for sonicated vesicles of 16% Ptd-L-Ser, the corresponding $K_D$ must be >0.2 nM to preserve the constraints on these parameters imposed by the standard binding model. These constraints are further discussed below in detail.

Figure 3B:
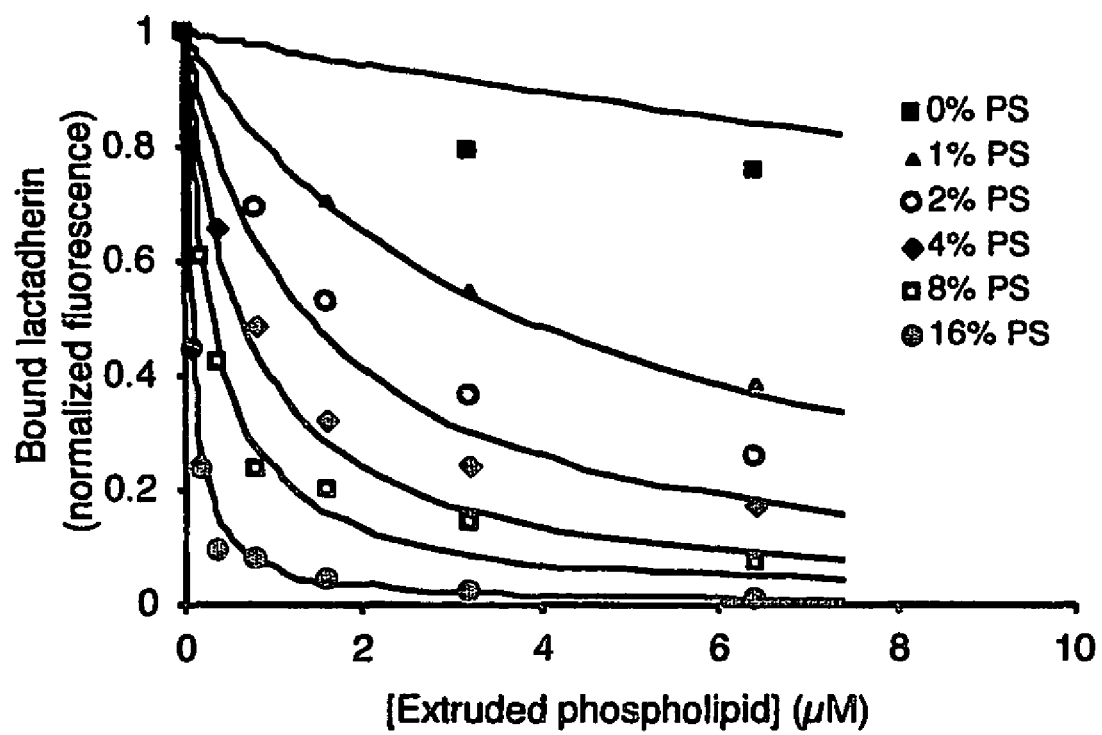

Extruded vesicles (nominal diameter 73±25 nm (Reference 39)) exhibited at least 4-fold fewer binding sites and the minimum possible $K_D$ was 4-fold higher (FIG. 3B). Large multilamellar vesicles (diameter >400 nm (Reference 42)) (FIG. 3C) exhibited the fewest binding sites. The ratio of phospholipid monomers/binding site was 30-fold higher than extruded vesicles (n≦6000). However, the maximum dissociation constant remained in the same range as the $K_D$'s for sonicated and extruded vesicles. This result indicates that, like factor VIII and factor V, lactadherin has a similar affinity for membranes with greatly varying curvature, but the number of phospholipid molecules per site can vary substantially.

Figure 3C:
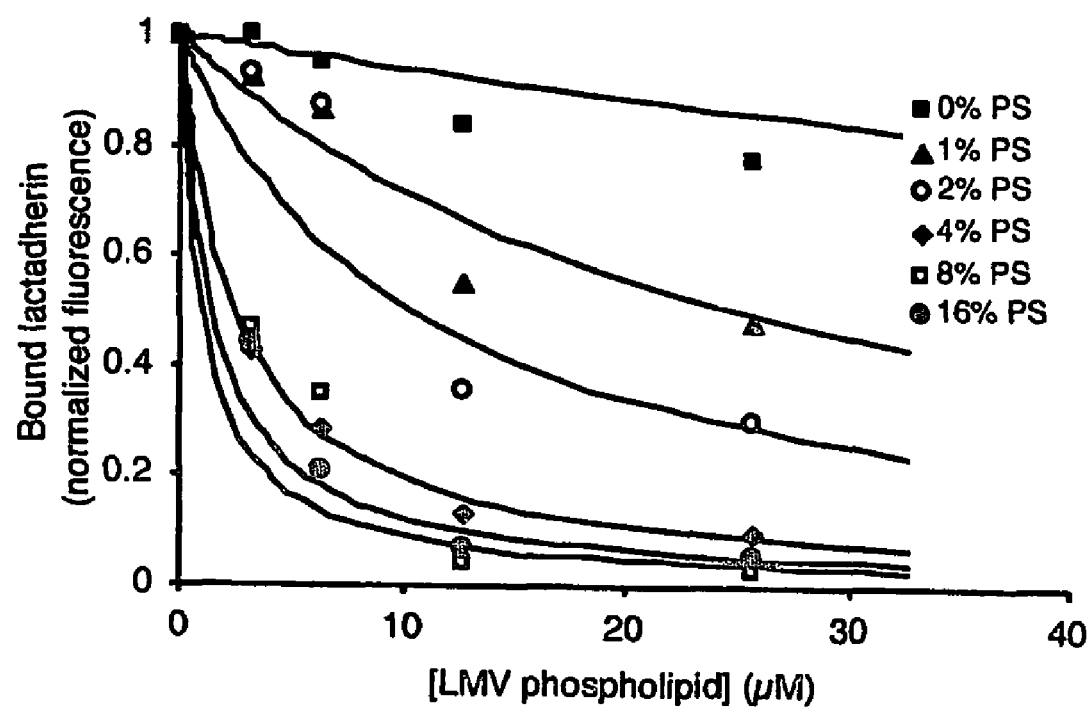
Figure 3D:
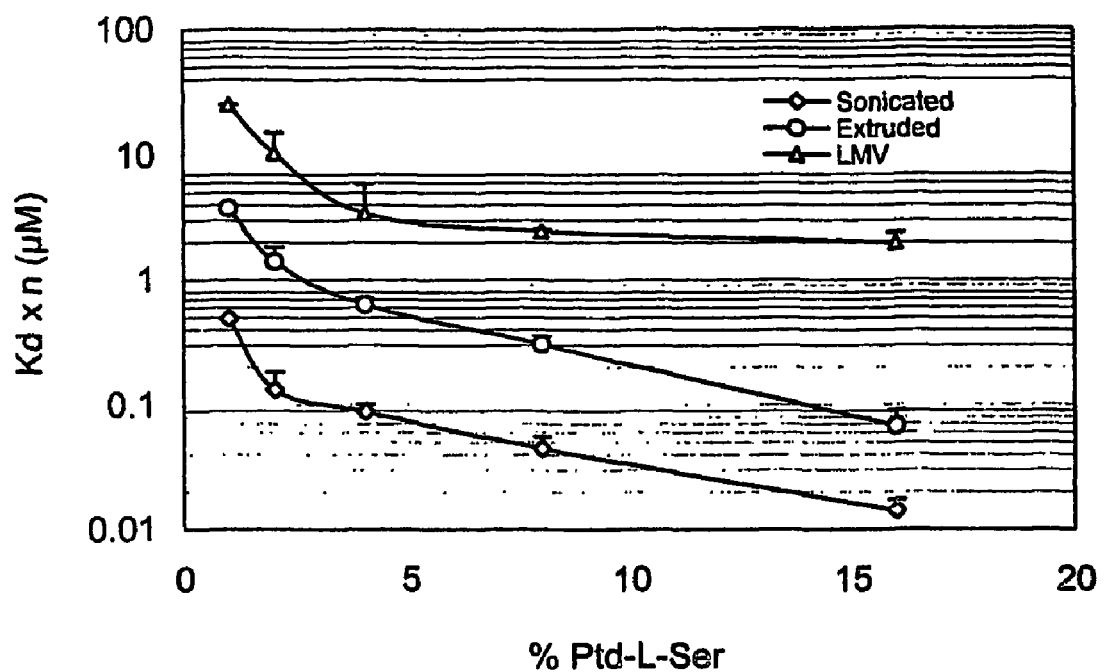

We used non-linear least squares curve fitting to model our competition binding data (FIG. 3A-C smooth curves). A composite parameter, $K_D \times n$, was utilized to fit the dissociation binding curves (FIG. 4D). Assuming that $K_D$ does not vary substantially with membrane curvature, as discussed above, the fitted curves indicate that sonicated vesicles may have as many as 10-fold more lactadherin bindings sites per phospholipid molecule than larger extruded vesicles. Extruded vesicles have approximately 10-fold more sites/phospholipid monomer than large multilamellar vesicles. For all vesicle types, the number of phospholipid monomers per binding site increases approximately 50-fold as the Ptd-L-Ser content drops from 16% to 1% with the steepest drop when Ptd-L-Ser≦2%

Figure 4A:
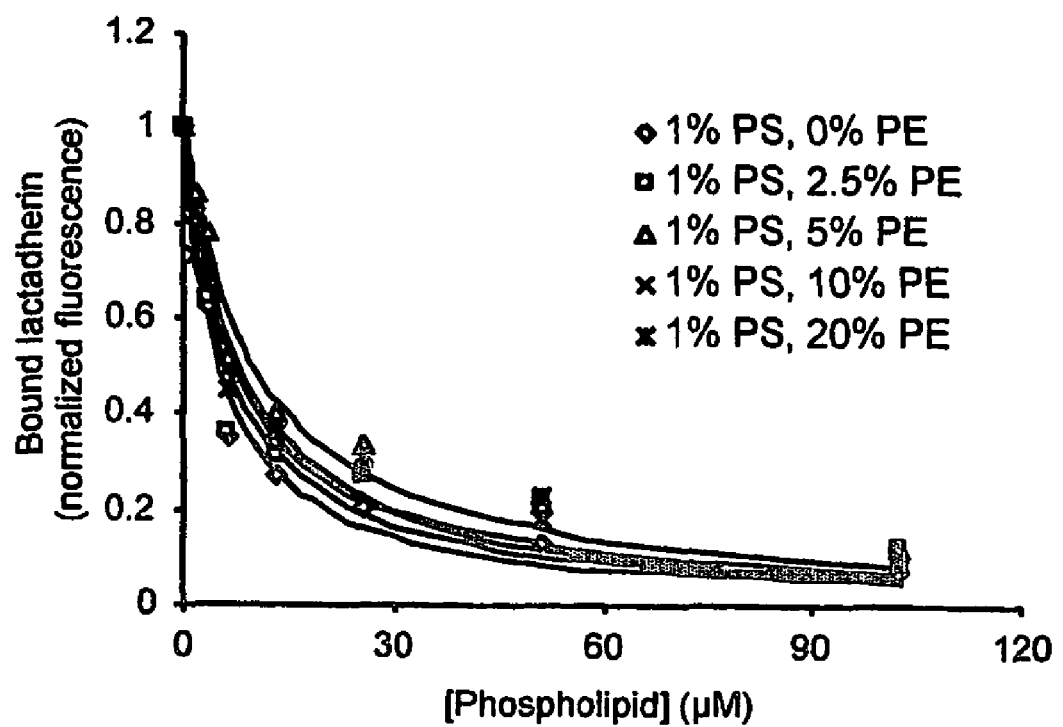
FIGS. 4A-C illustrate the relationship of membrane PE content, lipid charge, and $Ca^{++}$ to lactadherin binding.

We determined whether PE enhances binding of lactadherin to membranes containing Ptd-L-Ser, as it does for factor VIII (FIG. 4A). Accordingly, we utilized extruded vesicles containing 0-20% PE and 1% Ptd-L-Ser for competition binding experiments. The PE did not influence the apparent number of binding sites or affinity for lactadherin. Thus, lactadherin differs from factor VIII in exhibiting high affinity binding that is independent of membrane PE content.

Figure 4B:
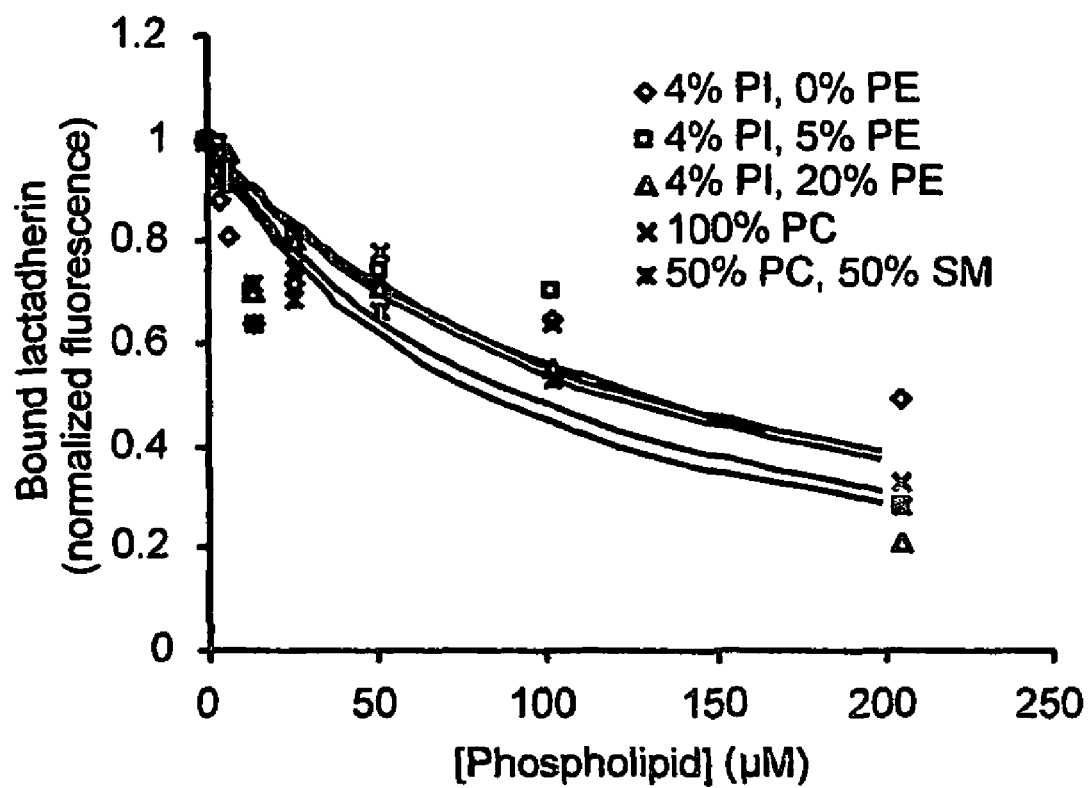

We determined whether a negatively charged phospholipid other than Ptd-L-Ser will support binding of lactadherin. Phosphatidylinositol was selected because it is the second most abundant anionic phospholipid of eukaryotic cells. Extruded vesicles with phosphatidylinositol competed with liposheres containing Ptd-L-Ser for binding of lactadherin (FIG. 4B). The results indicated that, although phosphatidylinositol is a negatively charged lipid, it does not support high affinity binding of lactadherin. PE did not alter the lack of efficacy for phosphatidylinositol in supporting high affinity binding of lactadherin.

All vesicles containing phosphatidylinositol supported low affinity binding of lactadherin (FIG. 4B). Control vesicles containing only PC or a mixture of PC and sphingomyelin also supported low affinity lactadherin binding. This indicated that neither phosphatidylinositol nor PE have a specific effect on membrane binding of lactadherin. Curve fitting analysis for vesicles lacking Ptd-L-Ser indicated that the product of $K_D \times n$ was at least 20-fold greater than for vesicles of comparable curvature containing 2% Ptd-L-Ser.

Figure 4C:
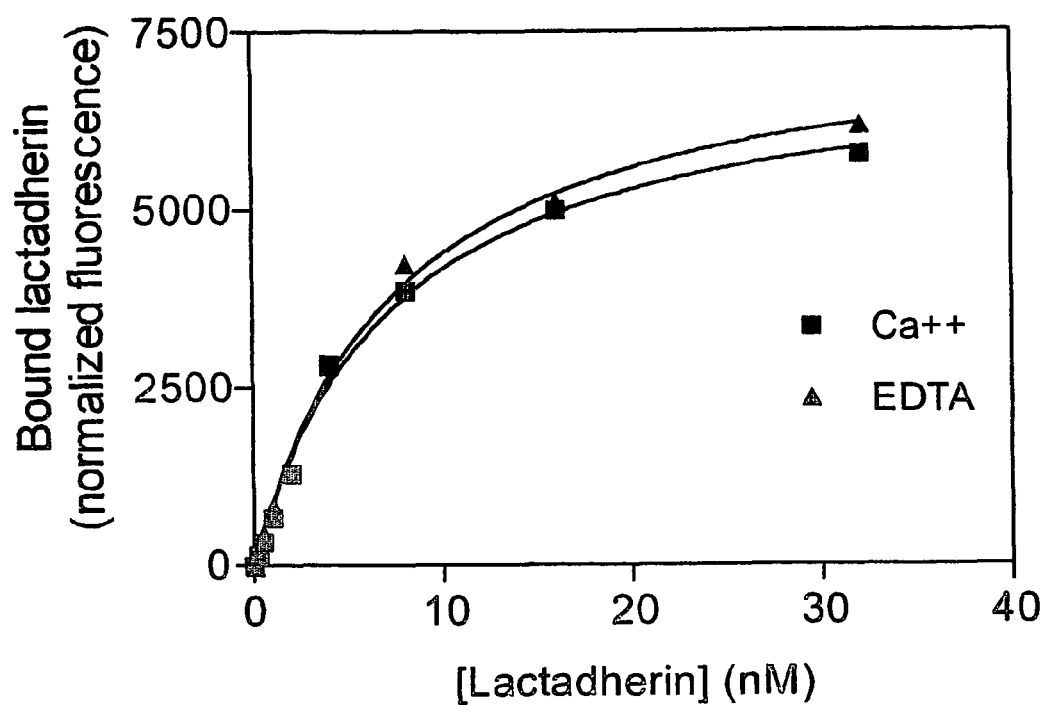

We determined whether $Ca^{++}$ influences membrane binding of lactadherin (FIG. 4C). The results indicated equivalent binding of lactadherin to membranes containing 4% Ptd-L-Ser in the presence of 1.5 mM $Ca^{++}$ vs. no $Ca^{++}$. These results indicate that lactadherin resembles factor VIII (unpublished observations) and factor V (Reference 43) in the characteristic of $Ca^{++}$-independent membrane binding.

Figure 5A:
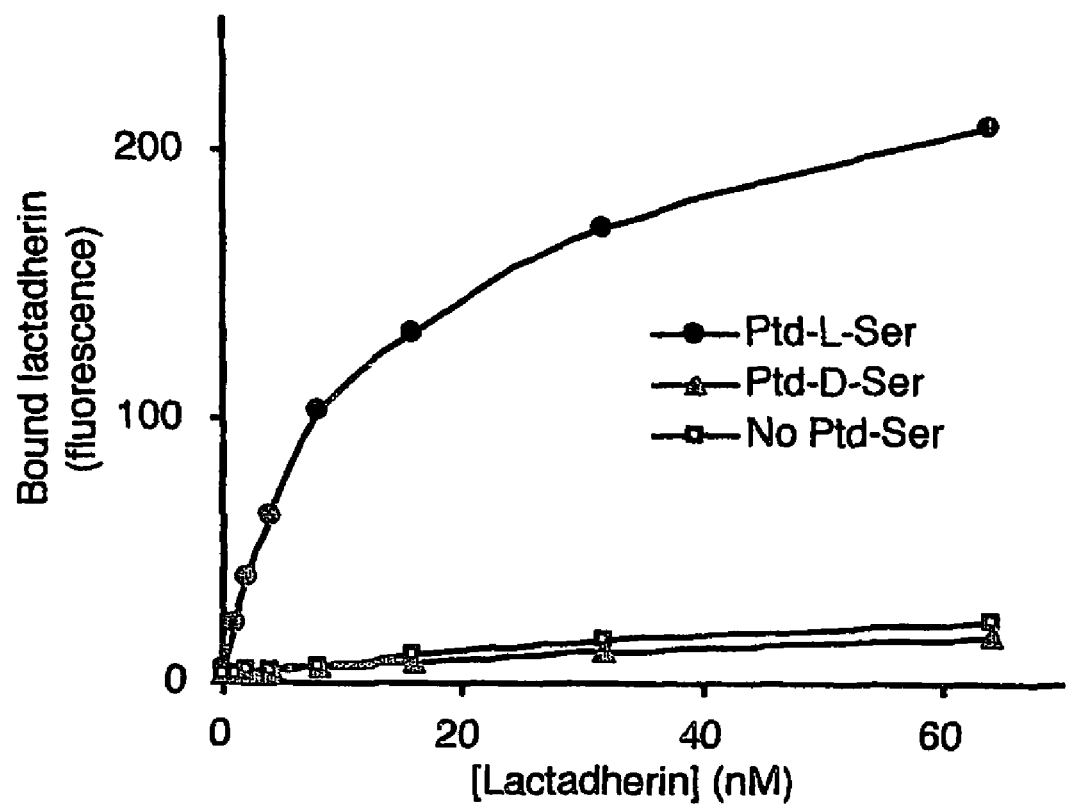
FIGS. 5A-B illustrate the relationship of lactadherin binding to the stereochemistry of Ptd-L-Ser.
Figure 5B:
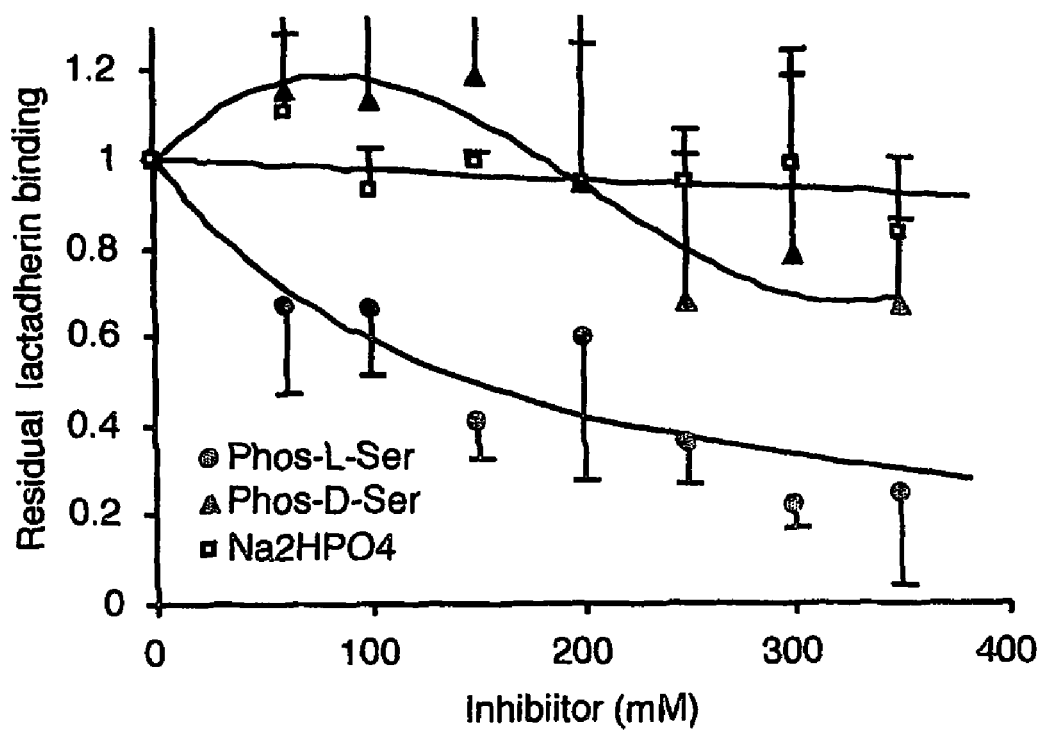

We determined whether lactadherin, like factor VIII and factor V, exhibits stereoselective preference for Ptd-L-Ser vs. Ptd-D-Ser (FIGS. 5A-B). Dioleoyl Ptd-D-Ser and control Ptd-L-Ser were synthesized by transphosphatidylation of dioleoyl PC. We mixed the synthetic Ptd-D-Ser or Ptd-L-Ser as 2% of total phospholipid with 20% PE and the balance as PC. The phospholipid mixture was hydrated and sonicated to form SUV as described above. These vesicles and control vesicles lacking Ptd-L-Ser or Ptd-D-Ser were used as a lipid source to prepare liposheres with which to evaluate the selectivity of lactadherin for Ptd-L-Ser.

Liposheres with membranes containing 2% synthesized dioleoyl Ptd-L-Ser bound lactadherin with high affinity, comparable to Ptd-L-Ser from biologic sources. Liposheres displaying synthesized 2% Ptd-D-Ser did not support binding of lactadherin above the level supported by control membranes of PE:PC 20:80 (FIG. 5A). These results indicate that lactadherin has a stereoselective affinity for Ptd-L-Ser, but that the affinity for Ptd-D-Ser does not exceed the affinity for PE.

To estimate the stereoselective affinity of lactadherin for the L-serine containing head group of Ptd-L-Ser, we performed binding inhibition studies (FIG. 5B). Phospho-L-Ser inhibited binding to liposheres with half maximal concentration of 160 mM. In contrast, phospho-D-serine caused a modest increase in membrane binding at low concentrations and was at least 4-fold less effective as an inhibitor. These results are consistent with stereoselective binding of lactadherin to Ptd-L-Ser, but indicate that additional lipid component(s) are necessary to support high affinity binding.

Figure 6:
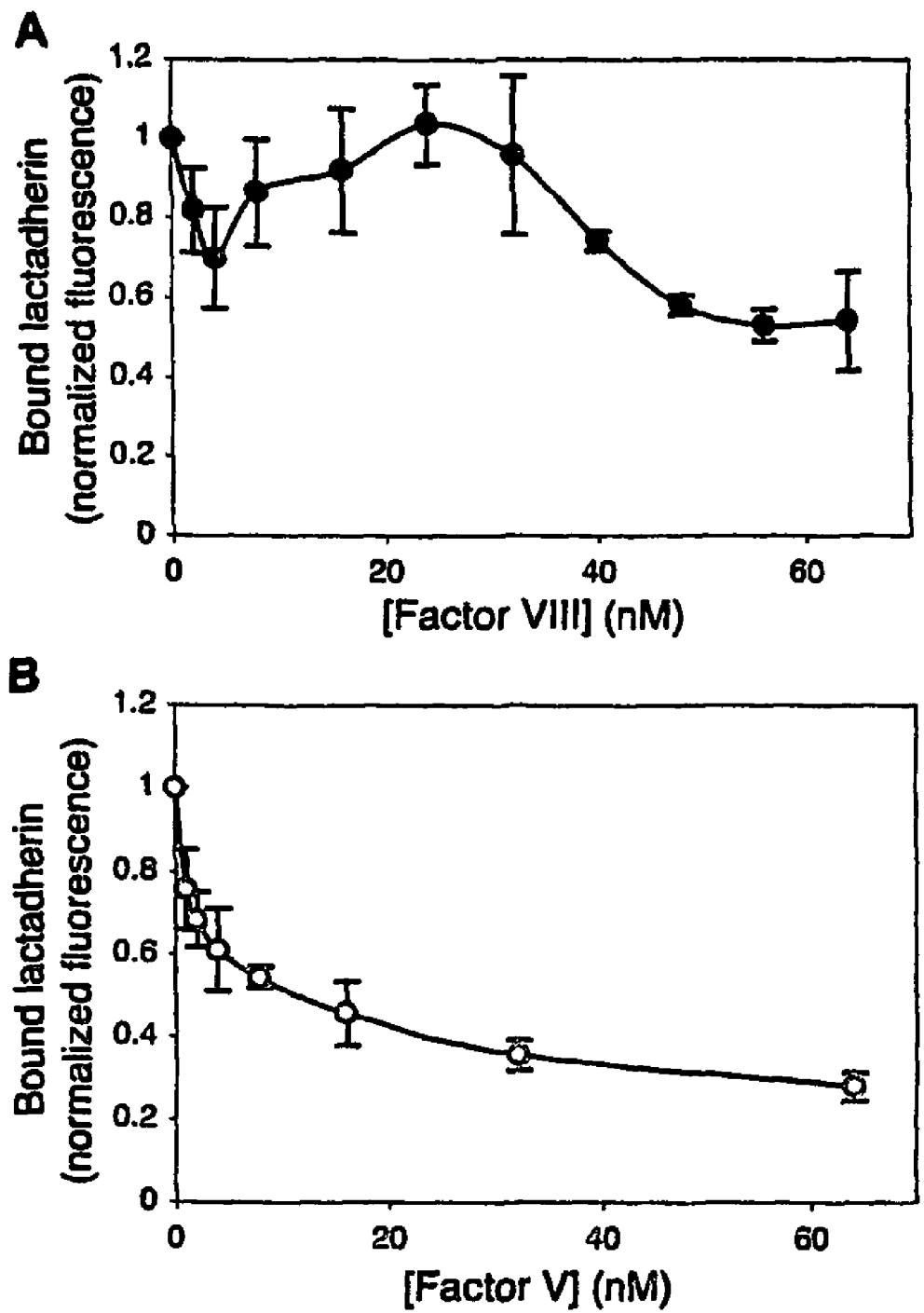
FIGS. 6A-B illustrate competition of factor VIII and factor V for lactadherin binding sites.

To explore the relationship between the phospholipid binding sites recognized by lactadherin vs. factor VIII or factor V, we performed competition binding experiments (FIGS. 6A-B). We determined whether factor VIII would compete with fluorescein-labeled lactadherin for binding to liposheres containing 4% Ptd-L-Ser (FIG. 6A). Ten minutes after liposheres were added, liposhere-bound lactadherin was evaluated by flow cytometry. Concentrations of factor VIII ranging from 0-4 nM displaced approximately 25% of bound lactadherin. However, intermediate concentrations of factor VIII, from 8-32 nM, led to increased lactadherin binding. Finally, concentrations from 40-64 nM factor VIII led to decreased lactadherin binding with a plateau of approximately 70% of original binding. Because the dissociation constant of factor VIII for liposheres of this composition is 4.8 nM, these results suggest that factor VIII participates in a low level of positive cooperative binding with lactadherin and competes for fewer than half of lactadherin binding sites. Results are mean±SD for 9 such experiments for FIG. 6A.

Factor V competed for approximately 70% of lactadherin binding sites. In contrast to factor VIII, there was no apparent cooperativity between factor V and lactadherin (FIG. 6B). Together, the competition binding experiments indicate that neither factor VIII nor factor V recognize all of the phospholipid binding sites recognized by lactadherin. Results represent two such experiments.

Our data identify membrane-binding properties of lactadherin that are both similar to and different from those of blood clotting factors VIII and V. Lactadherin exhibits specificity for Ptd-L-Ser and high affinity for membrane binding sites similar to factors VIII and V. Also, lactadherin recognizes many more binding sites on membranes that are highly curved as opposed to the more planar membranes found in larger vesicles (References 21 and 44). In contrast to factor VIII, but with similarity to factor V, lactadherin recognizes many binding sites on membranes with a Ptd-L-Ser content of less than four percent. Lactadherin differs from factor VIII in binding which is independent of membrane PE content (Reference 21).

Our discovery builds upon published data demonstrating that lactadherin binds preferentially to phosphatdylserine. Prior reports indicated that lactadherin binds to purified Ptd-L-Ser absorbed to a plastic surface (References 4, 6 and 27). Our data demonstrates stereoselective preference for the L-serine enatiomer of phosphatidylserine, indicating that lactadherin binds when the Ptd-L-Ser content of a membrane is in the physiologic range, and reporting the affinity of lactadherin for Ptd-L-Ser in a bilayer (References 17 and 45).

Ptd-L-Ser is a diastereomer rather than a stereoisomer of Ptd-D-Ser and we considered the possibility that different physical properties of the diastereomers might influence phospholipid affinity of lactadherin. Ptd-L-Ser has chiral centers at both the α-carbon of serine and the β-carbon of the glycerol backbone. As such, Ptd-D-Ser has different physical properties than Ptd-L-Ser. For example, pure preparations of the two phospholipids undergo phase transitions between $L_\beta$ and $L_\alpha$ phases at temperatures that differ by 0.4° C. (Reference 46). Thus, lactadherin's selectivity for membranes containing Ptd-L-Ser could be a consequence of the physical properties of Ptd-L-Ser rather than chemical recognition of the phospho-L-serine head group by lactadherin. This explanation seems unlikely for two reasons. First, when Ptd-L-Ser and Ptd-D-Ser are dispersed in phospholipid bilayers the measurable physical properties are not easily distinguishable. For example, clustering of Ptd-L-Ser in response to $Ca^{++}$ is not measurably different than clustering of Ptd-D-Ser (Reference 46). Second, our experiments with phospho-L-serine vs. phospho-D-serine indicated that lactadherin interacts selectively with the phospho-L-serine moiety (FIG. 5B). Thus, we believe the most likely explanation for selective binding of lactadherin to membranes with Ptd-L-Ser is a stereoselective binding of lactadherin to Ptd-L-Ser that includes selective binding to the phospho-L-serine moiety.

SUV's expose a smaller quantity of Ptd-L-Ser on their outer surface compared to PC and a larger quantity on the inner surface (References 47 and 48). The proportion of Ptd-L-Ser to PC in the outer membrane leaflet may be reduced by 60% when the Ptd-L-Ser content is ≦5% total lipid, and by 50% when the Ptd-L-Ser content is ≦10% (Reference 48). The asymmetric distribution of Ptd-L-Ser apparently results from the high level of curvature strain in SUV's, which also produces asymmetric distribution of PE and PC (References 49-52). Thus, while Ptd-L-Ser exposure on vesicles with the exact compositions used in these studies has not been measured, our SUV's probably displayed less Ptd-L-Ser in the outer membranes than the overall SUV composition suggests. The implication for these studies is that curvature strain per se may enhance binding site expression to a greater degree than our analysis suggests, offsetting the reduced exposure of Ptd-L-Ser in the outer membrane leaflet.

The physiologic relevance of lactadherin's preference for curved membranes may become evident in additional studies. We feel that lactadherin may bind preferentially to convex cell surfaces such as pseudopods, or plasma membrane vesicles such as those that enclose milk fat droplets. Another possibility is that in vivo lactadherin may induce membrane curvature rather than respond to it. For example, lactadherin that is secreted into the mammary duct could bind to plasma membrane Ptd-L-Ser or to a protein receptor of mammary epithelial cells and induce regions of convexity.

The limited capacity of factors VIII and V to compete with lactadherin for membrane binding sites implies that these proteins recognize distinct binding sites that do not overlap completely with those of lactadherin. For clarity, we will use the term "contact site" to specify the actual phospholipid clusters that interact with lactadherin from the usage of "binding site" elsewhere herein. The data in this report, combined with prior reports about factor VIII and factor V, places some constraints upon the characteristics of these contact sites. For example, the contact sites are probably not larger than 40-50 phospholipid molecules with 20-30 molecules in the membrane leaflet facing the binding protein (FIG. 3 and the accompanying text in the Results section above). The sites for factor VIII is probably contain more than one Ptd-L-Ser molecule while those for factor V and lactadherin may contain a single Ptd-L-Ser molecule. (Reference 20). Factor VIII and factor V do not compete efficiently with each other for contact sites indicating that the exact configuration of phospholipid molecules that either protein recognizes is distinct and that the arrangement of phospholipids is already present on the membrane when binding occurs (References 17 and 37). In contrast, lactadherin competes for all the contact sites recognized by both factor VIII and factor V (Reference 12). This suggests that lactadherin is the least fastidious of the three proteins in its contact site requirements.

Lactadherin's membrane-binding requirements contrast sharply with those of annexin V. While both proteins bind preferentially to Ptd-L-Ser-containing membranes, the relationship between Ptd-L-Ser content and number of binding sites is distinct. Lactadherin exhibits a steep positive relationship between Ptd-L-Ser content and number of binding sites over the range of 0-2% Ptd-L-Ser. In contrast, the relationship for Annexin V is sigmoidal with very few binding sites for a composition of less than 4% Ptd-L-Ser at physiologic $Ca^{++}$ concentrations and a steep rise with Ptd-L-Ser content above that level (References 53 and 54). Lactadherin binds preferentially to regions of sharp curvature while Annexin V binds preferentially to flat membrane patches (Reference 55). Annexin V requires $Ca^{++}$ and has enhanced binding when PE is present (Reference 56). Lactadherin is independent of $Ca^{++}$ and PE. Annexin V molecules self-associate on the membrane leading to a cooperative binding (Reference 57). A consequence of the different membrane requirements is that annexin V exhibits limited capacity to inhibit the factor Xase or the prothrombinase complexes unless the Ptd-L-Ser content is high and the phospholipid vesicles have a large diameter (Reference 12). In contrast to annexin V, lactadherin inhibits both enzyme complexes over the range of phospholipid compositions and vesicle curvatures which support enzymatic activity.

Annexin V has found usage as a detector of cells that express surface Ptd-L-Ser (References 29 and 58). Our data predict that lactadherin might serve as a Ptd-L-Ser probe that is complementary to annexin V. The two proteins might bind to different cells or regions of cells that express Ptd-L-Ser. Annexin V binds to apoptotic cells where the phospholipid asymmetry between the inner and outer leaflets of the plasma membrane has collapsed. In contrast, annexin V does not bind to undifferentiated cells or malignant cells, that express sufficient Ptd-L-Ser to support activity of the prothrombinase and factor Xase complexes (Reference 59). If lactadherin successfully identifies immature cells, malignant cells, or certain cellular appendages then it is also plausible that lactadherin or the lectin domain(s) of homologous proteins could serve as pharmacologic targeting modules to identify or direct therapeutic agents to the Ptd-L-Ser-displaying cells.

Figure 7A:
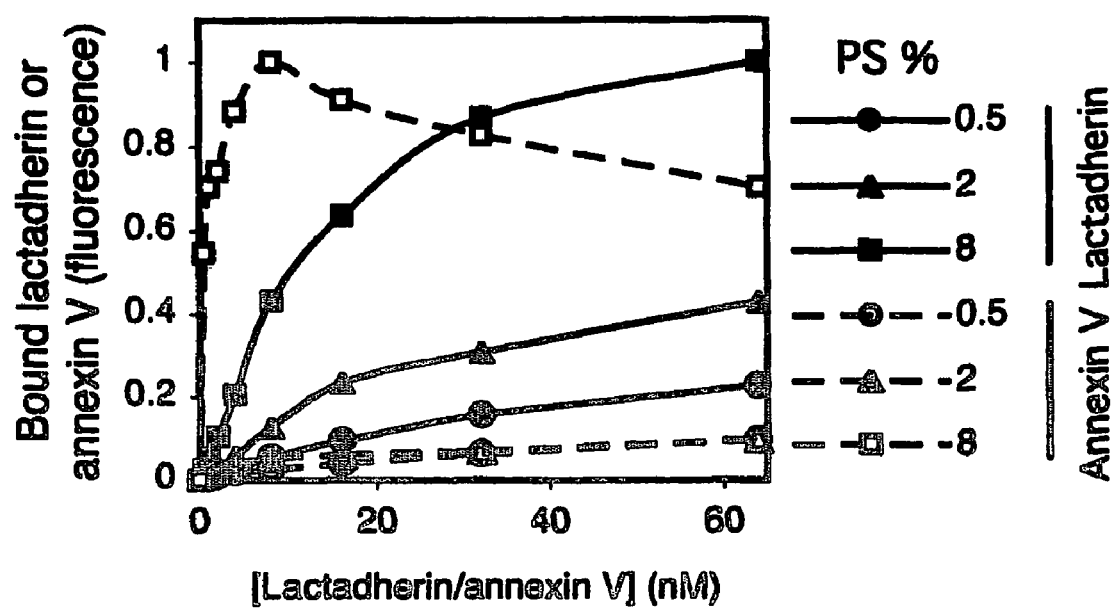
FIGS. 7A-D illustrate the relationship between membrane composition and binding of lactadherin and annexin V. FIG. A—Fluorescein-labeled lactadherin (closed symbols) or annexin V (open symbols) at various concentrations, was mixed with liposheres.

We hypothesized that lactadherin could be utilized as a PS probe on physiologic membranes with less than 4% PS. Our hypothesis was based on the observation that the number of lactadherin binding sites on synthetic membranes is approximately proportional to the PS content. In contrast, annexin V requires a threshold membrane PS content of greater than 1% before membrane binding is detectable (Reference 54), We performed preliminary experiments to confirm the differential relationship of lactadherin vs. annexin V (FIG. 7A). Synthetic membranes of, 0.5%, 2%, 8% were supported by glass microspheres (lipospheres). Membranes had the indicated PS content with a PS:PE ratio of 1:4 and the balance as phosphatidylcholine Bound lactadherin or annexin V was evaluated by flow cytometry after 10 min. Fluorescence values are normalized to the maximum fluorescence value for membranes of 8% PS Bound fluorescein-lactadherin or annexin V was evaluated by flow cytometry after 10 min. The results confirmed that the number of lactadherin binding sites is proportional to PS content while annexin V requires a threshold PS content greater than 2% (FIG. 7A).

Figure 7B:
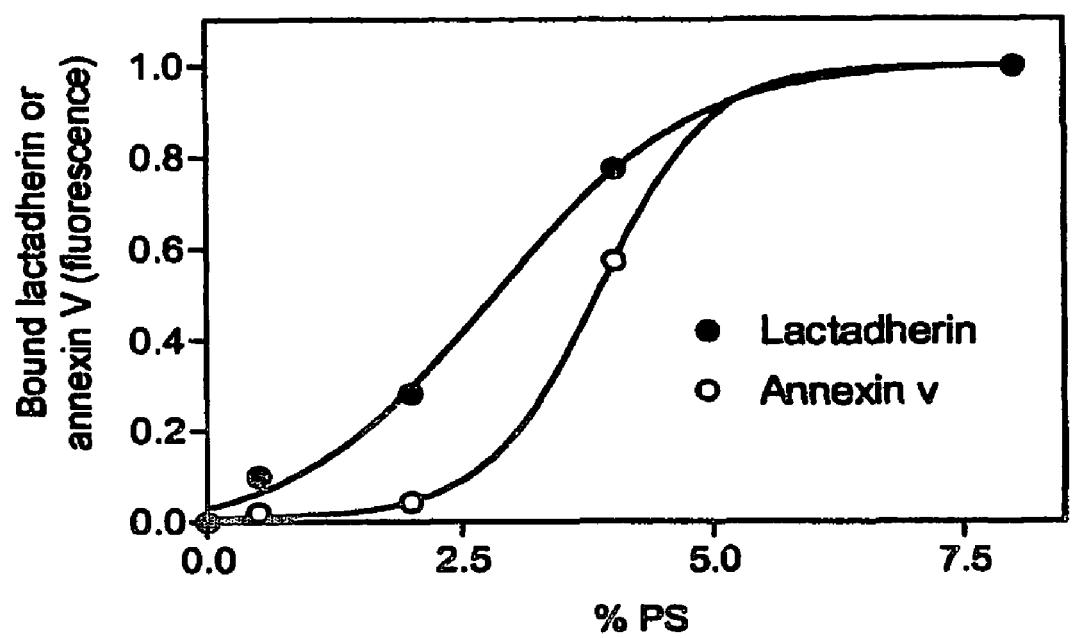

The quantity of lactadherin or annexin V bound to lipospheres was compared as the PS content varied. The concentration of either protein was fixed at 4 nM (FIG. 7B). The results confirmed a near-linear relationship between number of lactadherin binding sites over a PS content range of 0-4%. In contrast, the relationship between the PS content and number of annexin V binding sites was sigmoidal. The threshold for detectable annexin V binding appeared to be approximately 2.5% PS.

Figure 7C:
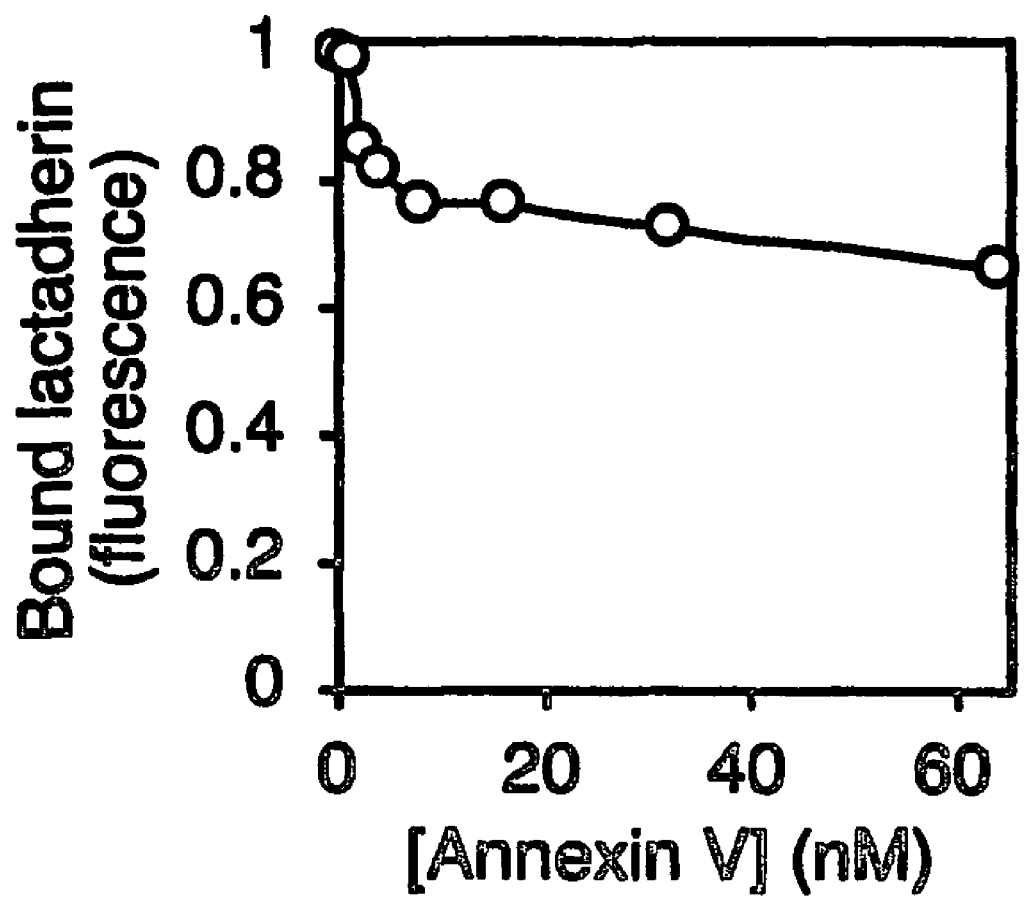
Figure 7D:
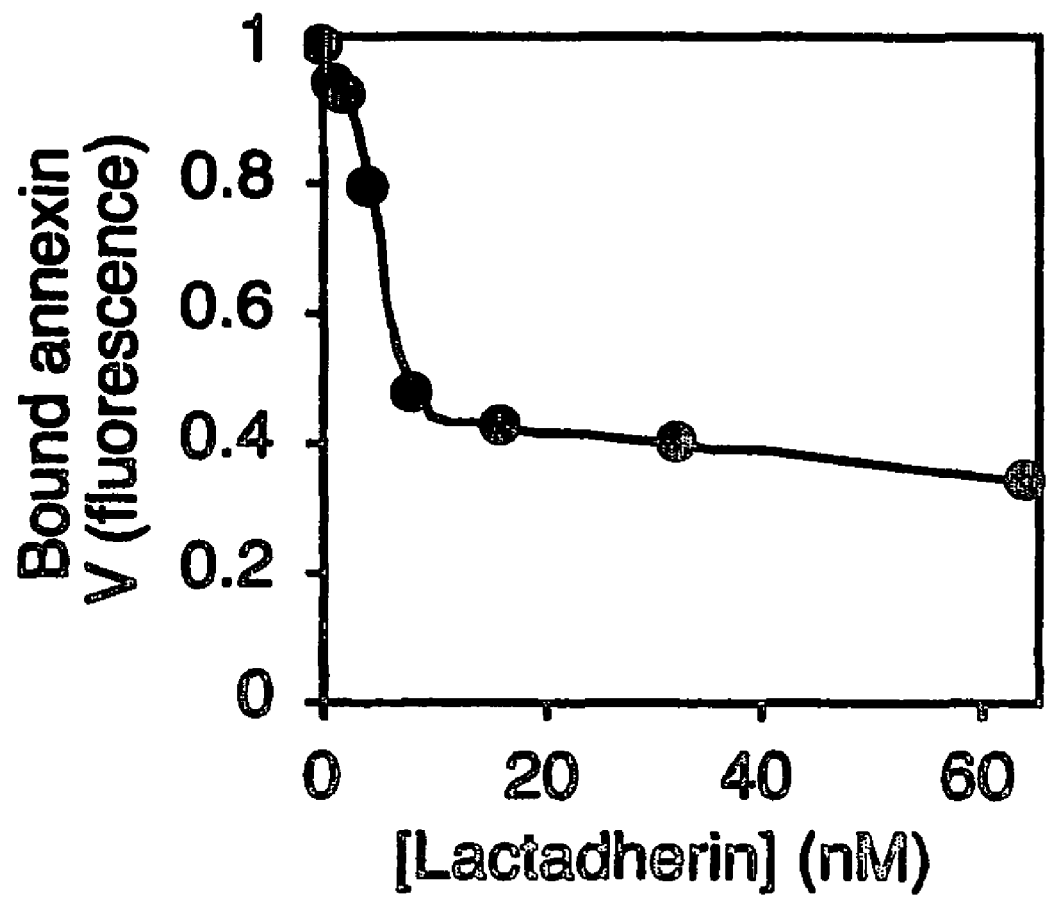

We performed competition binding experiments to determine whether lactadherin and annexin V could compete with the other for the same binding sites (FIG. 7C). Fluorescein-labeled lactadherin, 4 nM, was mixed with various concentrations of unlabeled annexin V prior to addition of lipospheres with 4% PS Unlabeled annexin V competed for only about 40% of the lactadherin binding sites on membranes with 4% PS. By comparison, unlabeled lactadherin competed for approximately 70% of binding sites of annexin V on membranes with 4% PS. (FIG. 7D) These results indicate that the binding sites for lactadherin and annexin V overlap but are not identical. They indicate, further, that the presence of either protein at low concentrations would not diminish the number of binding sites detected by the other more than 50%.

Figure 8A:
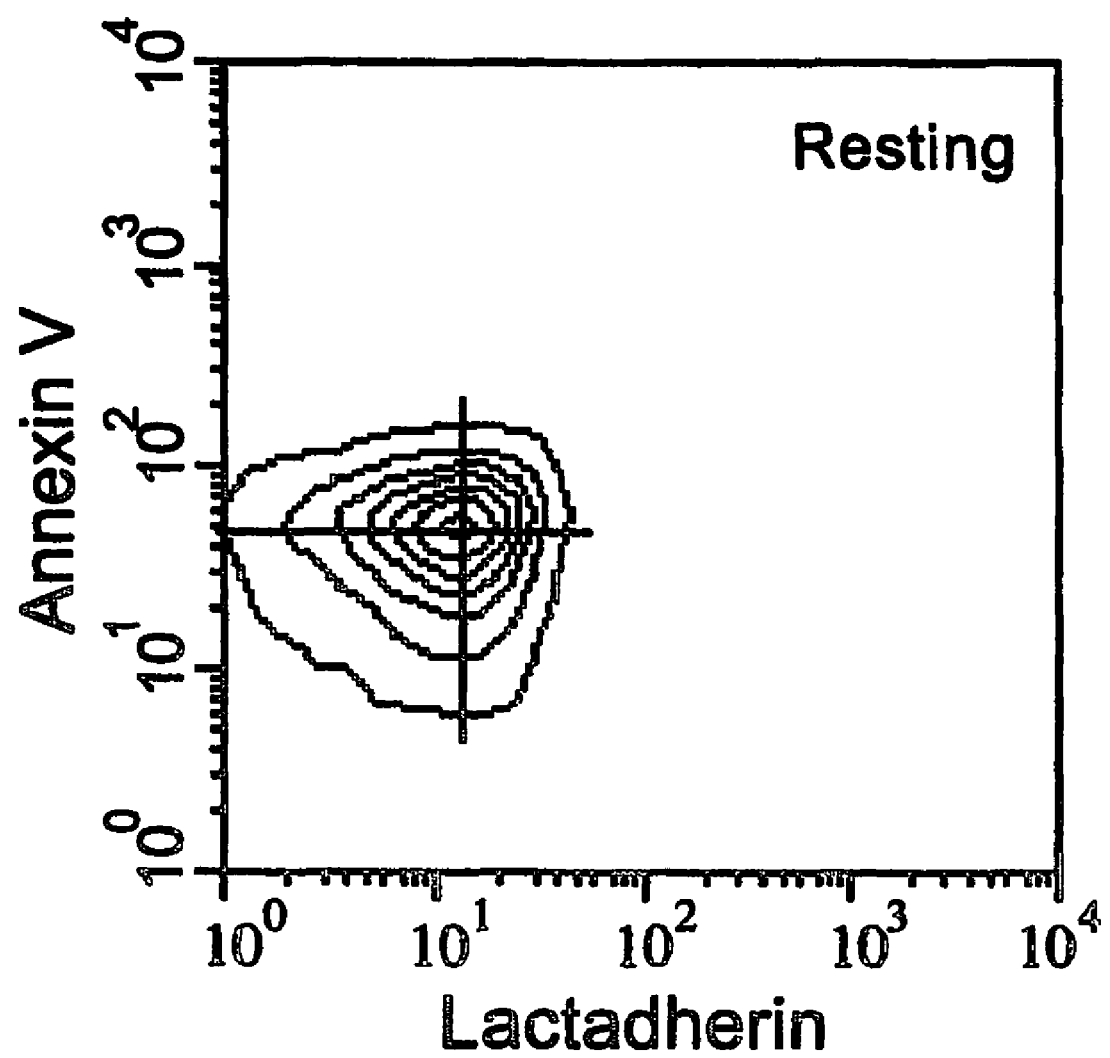
FIGS. 8A-C illustrate expression of lactadherin and annexin V binding sites on platelets stimulated with A23187.
Figure 8B:
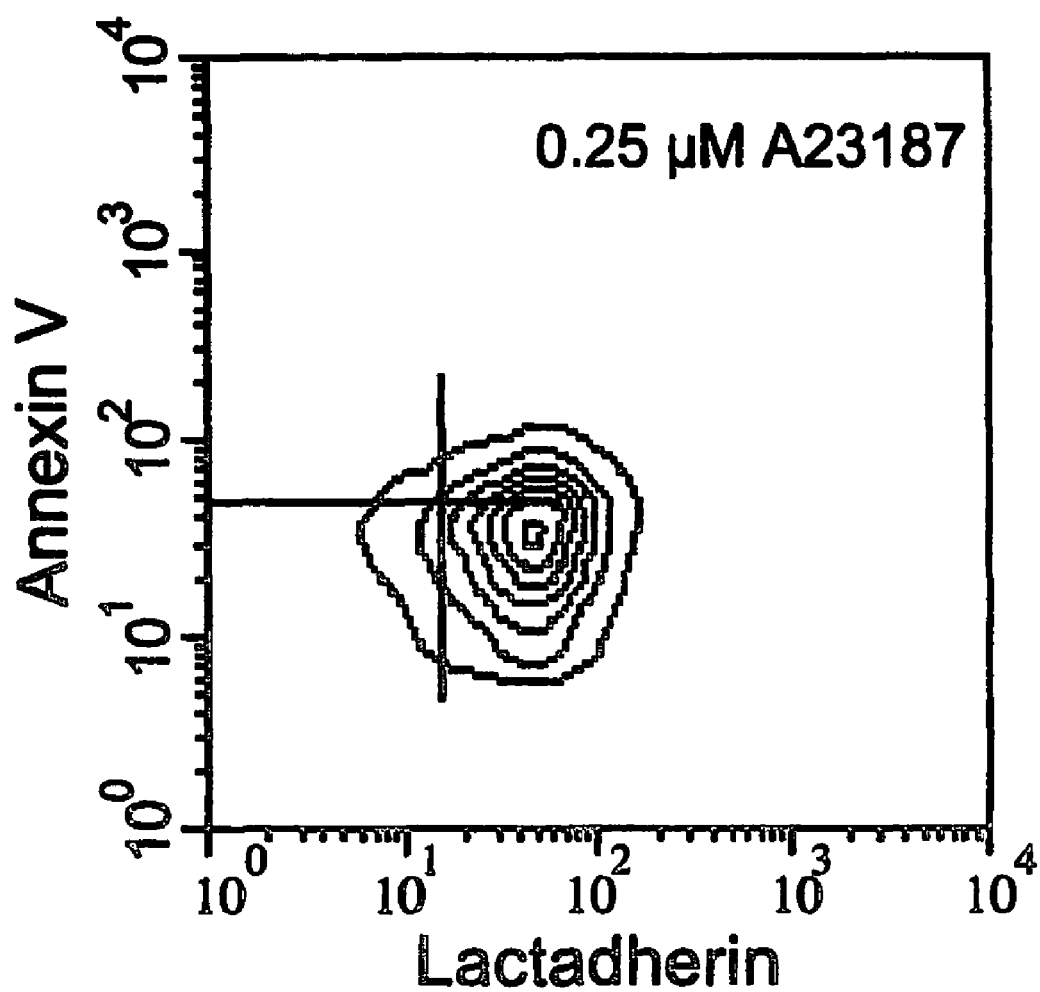
Figure 8C:
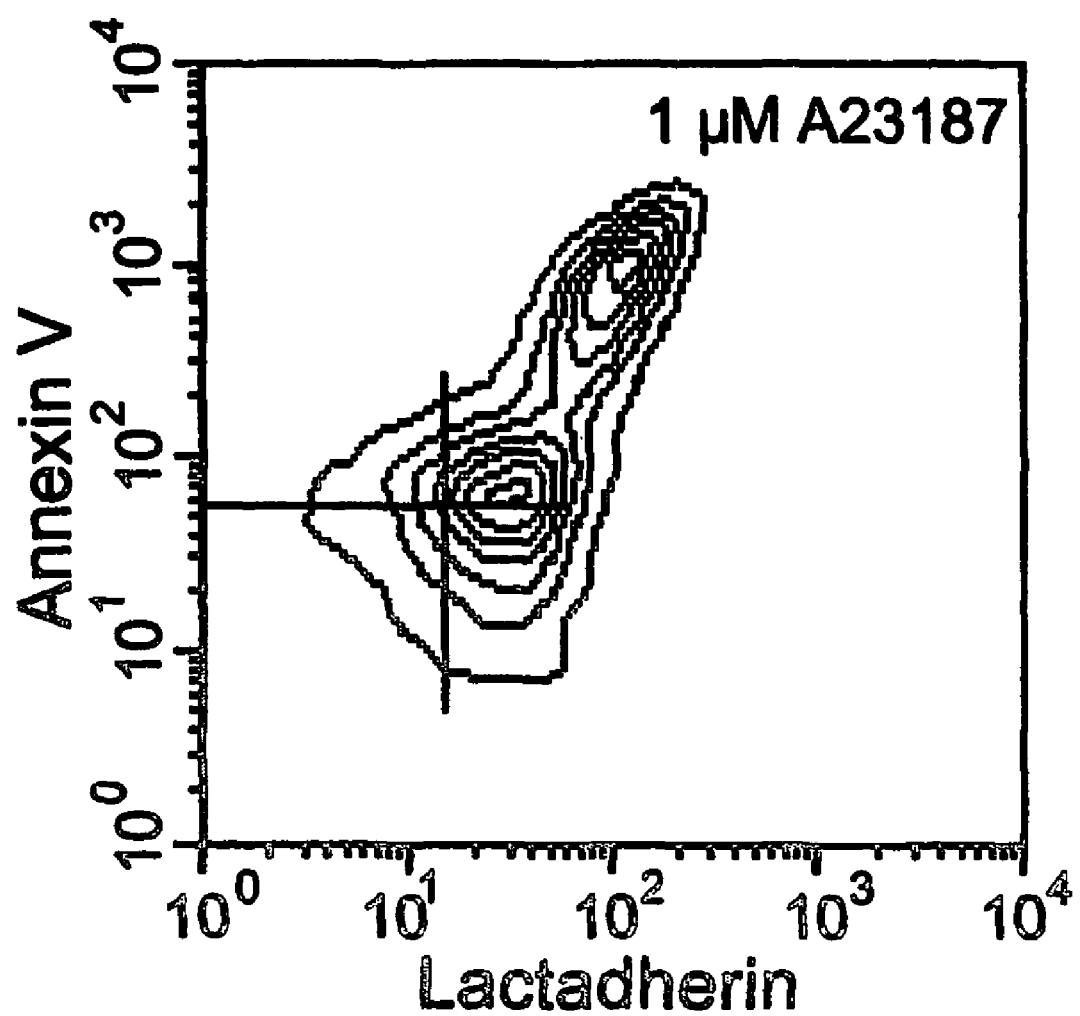

We asked whether platelets have a stimulated state when they bind lactadherin but not annexin V, consistent with the hypothesis that platelets have the capacity to regulate PS exposure at a level less than 2.5% PS (FIG. 8A-C). Platelets were incubated with fluorescein labeled lactadherin and Alexa Fluor 647 labeled annexin V. Because competition of either protein for the other's binding sites was <20% at these concentrations (FIG. 7C, 7D) we utilized both proteins simultaneously. The gain on the flow cytometer was set so that the intrinsic fluorescence of unstimulated platelets placed the population in the lower left quadrant of the display (FIG. 8A). Following stimulation by 0.25 µM calcium ionophore (A23187-Sigma) platelet binding of lactadherin increased while the binding of annexin V did not. Comparison with the unstimulated state indicates a net increase of fluorescence to approximately 3-fold. (FIG. 8B). The cross-hair allows comparison of modal fluorescence values for resting platelets vs. stimulated platelets.

When the A23187 concentration was increased to 1 µM, approximately half of the platelets remained in the left lower quadrant, with increased bound lactadherin but no increase in bound annexin V. The other half of the platelets were stimulated by this A23187 concentration to bind much more lactadherin and also annexin V. (FIG. 8C). When the A23187 concentration was increased to 2 µM all of the platelets expressed many lactadherin and annexin V binding sites, equivalent to the upper population in FIG. 8C. These results are consistent with an interpretation that platelets exposed to 0.1-0.5 µM A23187 increase membrane PS to a maximum <2.5% PS but that a concentration of A23187>1 µM leads to additional PS exposure that reaches a maximum >2.5%. Lines on contour plots indicate 20% linear increments of maximum event density. Displayed panels are from single experiments, representative of ten such experiments.

Figure 9A:
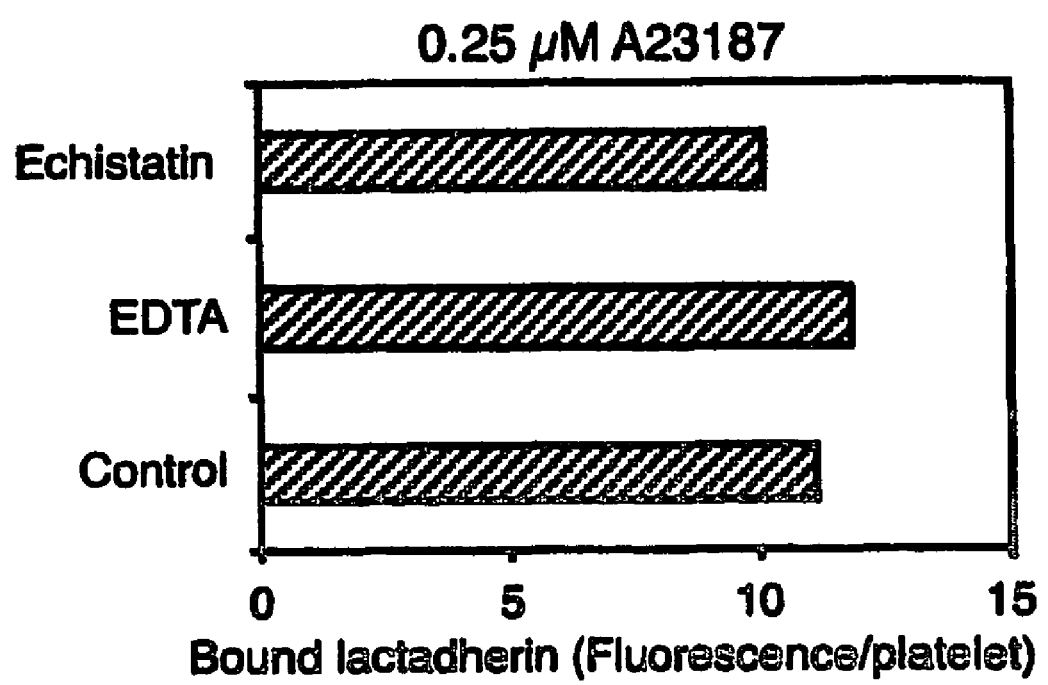
FIGS. 9A-F illustrate the relationship of binding sites for lactadherin to the phospholipid-binding C2 domain and to the integrin-binding EGF domain. Platelets were stimulated by 0.25 μM A23187 (FIGS. A, C, E) or 10 μM A23187 (FIGS. B, D, F) as described (FIGS. A, B)
Figure 9B:
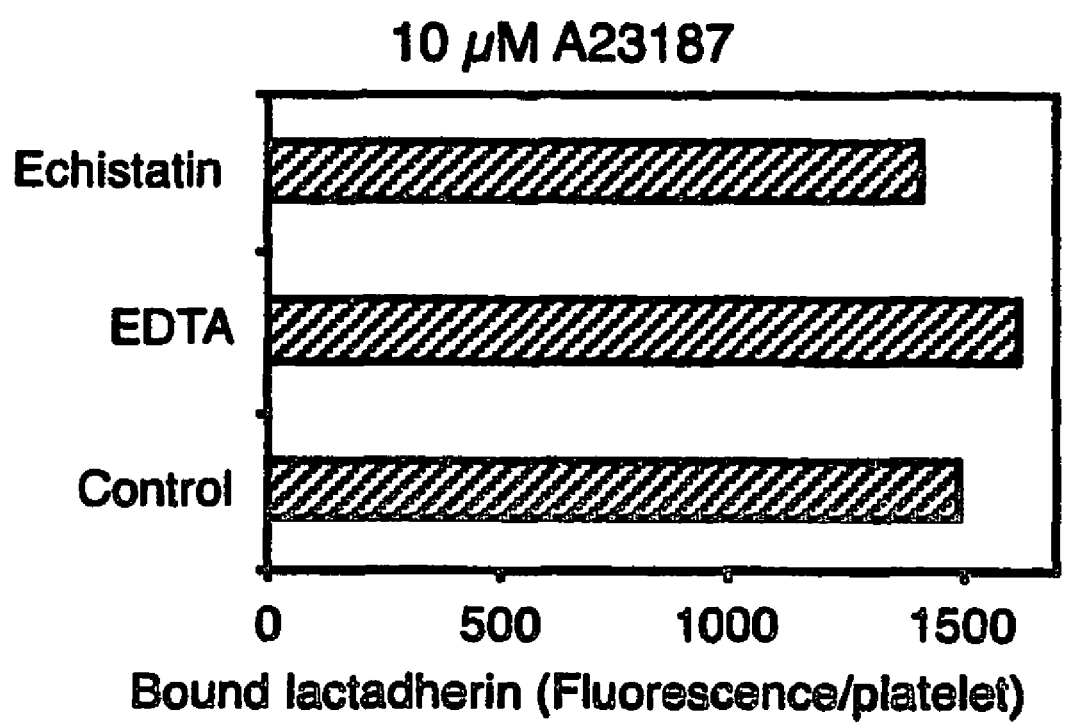

In order to confirm that binding of lactadherin to platelets was not mediated by the RGD-containing EGF motif, we performed binding experiments under conditions that prevent integrin binding of lactadherin (Reference 6). Fluorescein-labeled lactadherin was mixed with platelets stimulated by A23187 in the present of 1.5 mM $Ca^{++}$. Data showed that neither EDTA nor echistatin affected binding of lactadherin to platelets stimulated with 0.25 µM or with 10 µM A23187 (FIGS. 9A and 9B). These results indicate that >90% of lactadherin binding to stimulated platelets is not mediated by RGD-integrin interaction.

Figure 9C:
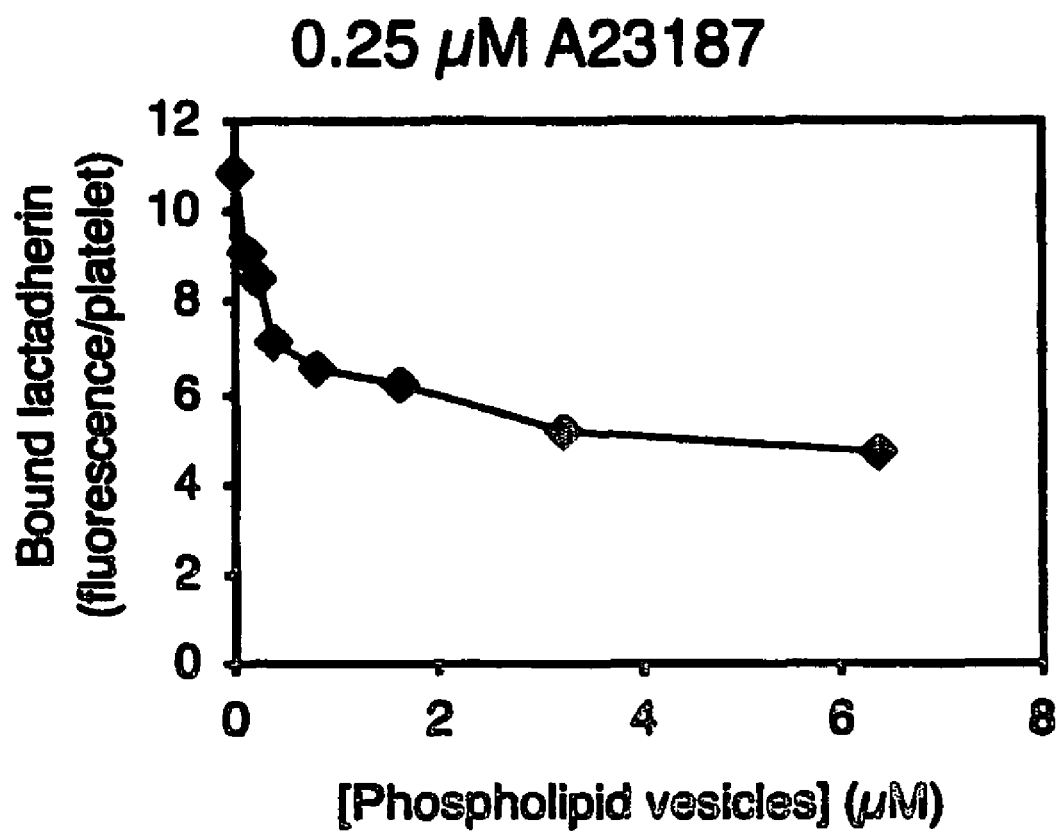
Figure 9D:
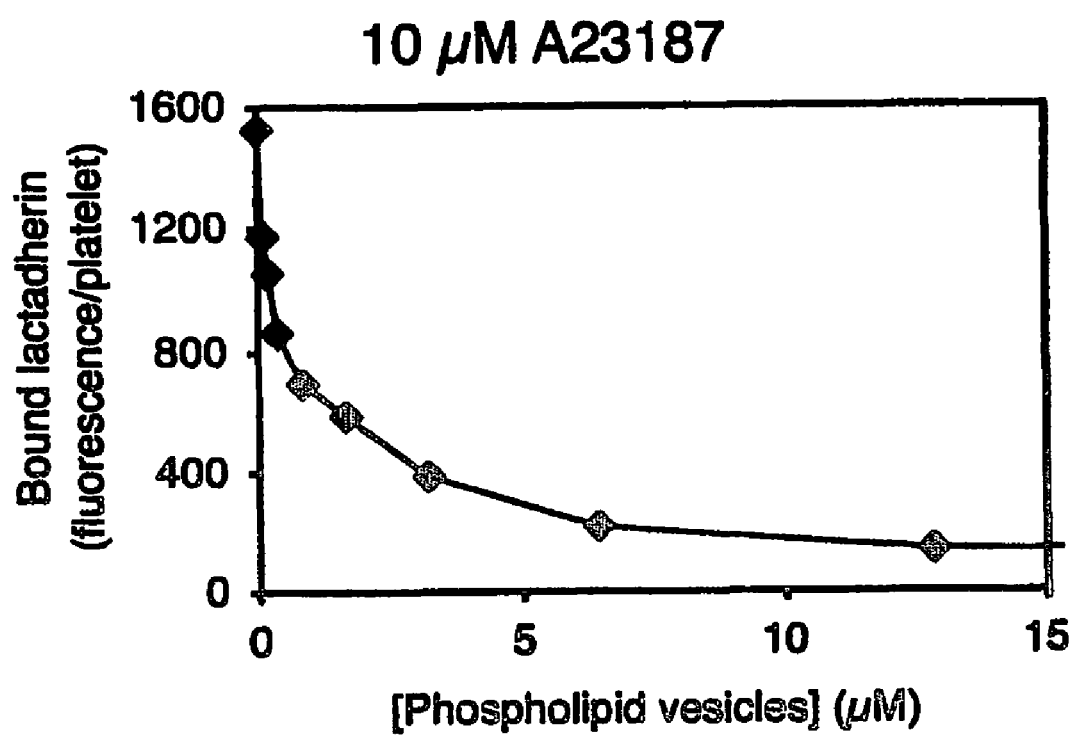

To confirm that lactadherin binds to stimulated platelets via the PS-binding C2 domain, we performed control experiments with PS-containing phospholipid vesicles and with a polyclonal antibody directed against lactadherin C2. PS-containing vesicles displaced more than 50% of lactadherin from platelets stimulated with 0.25 µM A23187 (FIG. 9C). Concentrations of sonicated vesicles at greater than 6 µM phospholipid led to increased binding of lactadherin to platelets (not shown). We attributed the increase to fusion of vesicles with platelets, thus depositing PS in the external membrane and possibly by perturbing the native phospholipid asymmetry in the course of vesicle-membrane fusion (References 60 and 61). PS-containing vesicles displaced >90% of lactadherin from platelets stimulated with 10 µM A23187 and there was no increase in lactadherin binding as the vesicles concentration increased (FIG. 9D). Fusion of PS-containing vesicles with the plasma membrane of these platelets is unlikely to significantly alter binding of lactadherin. A polyclonal antibody directed against the lactadherin C2 domain inhibited lactadherin binding to platelets by >80% for platelets stimulated at 0.25 and at 10 µM A23187. These results confirm that lactadherin binds to stimulated platelets via the PS-binding motif of the C2 domain.

Figure 10A:
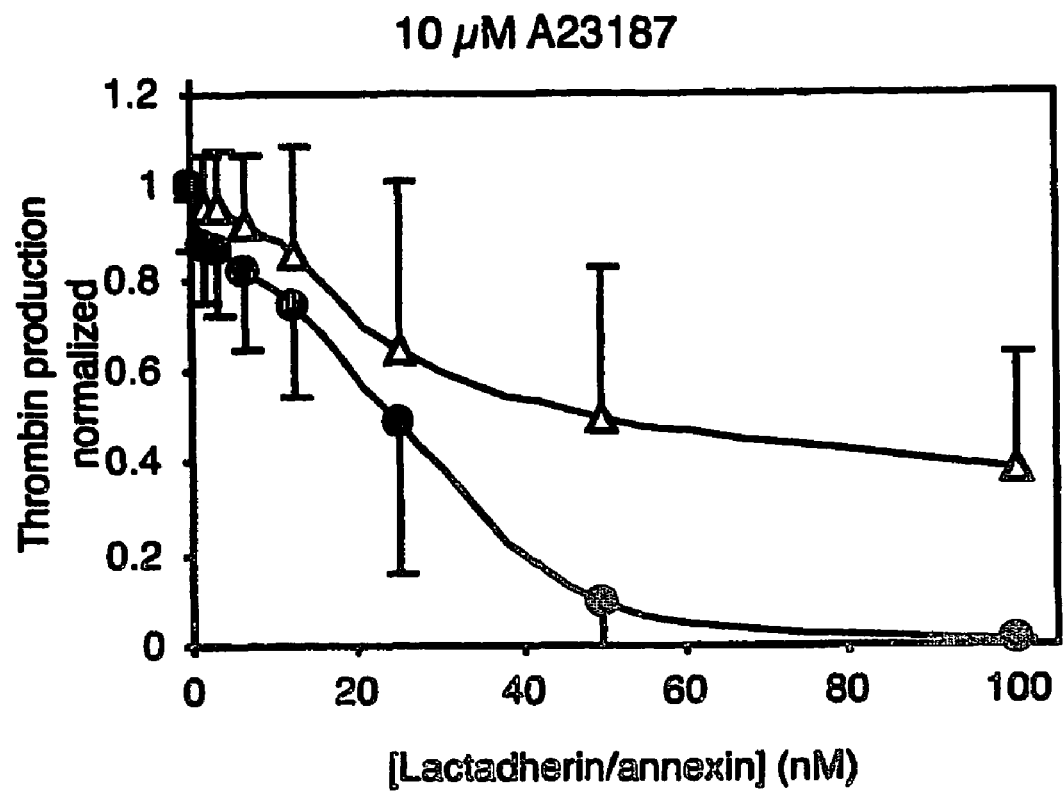
FIG. 10A-D illustrate inhibition of factor Xa and prothrombin production by lactadherin or annexin V on platelets stimulated by A23187.
Figure 10B:
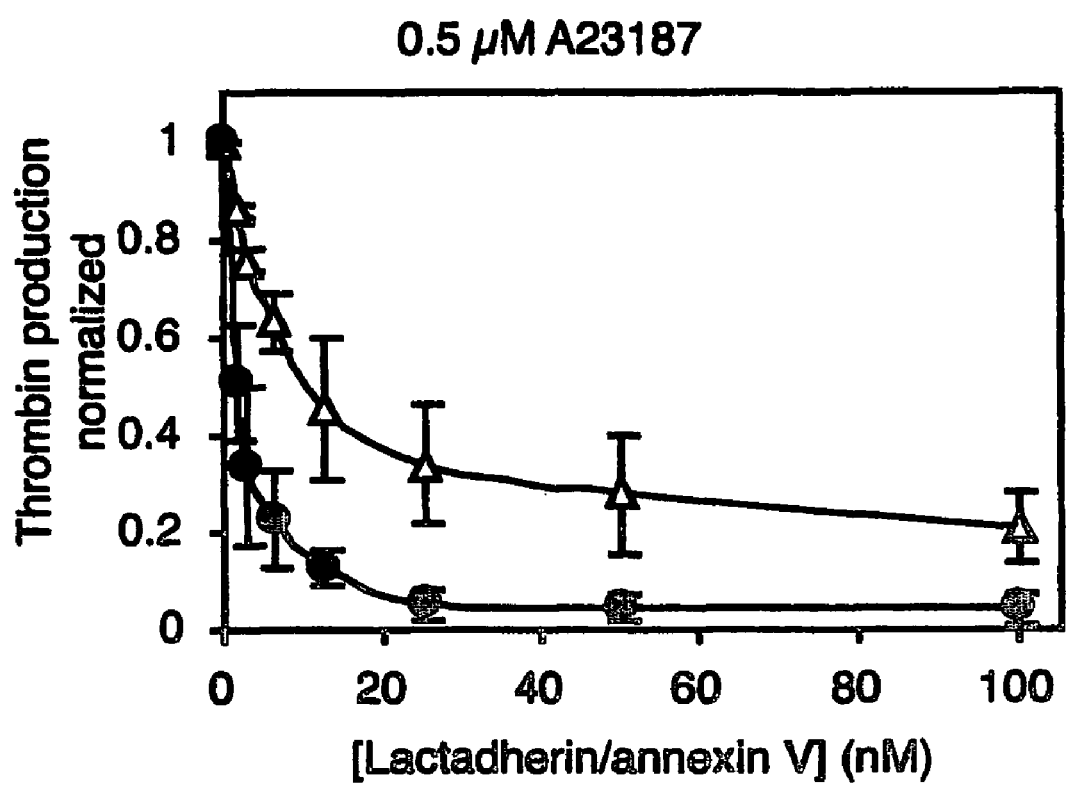
Figure 10C:
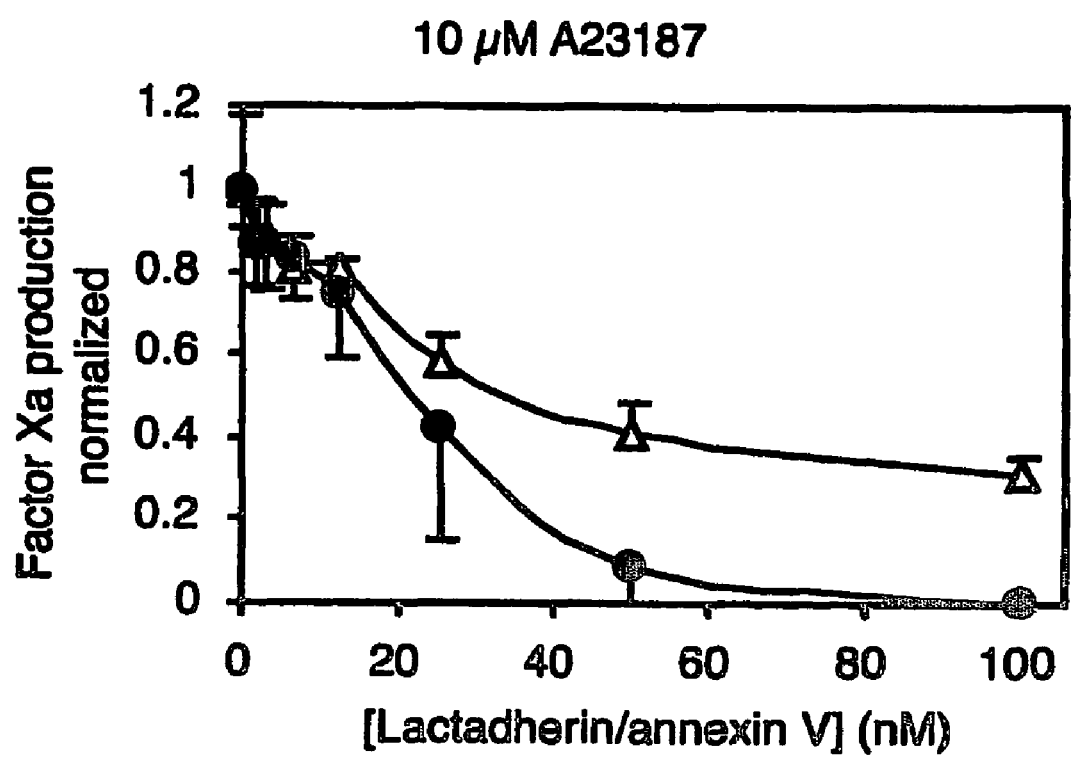
Figure 10D:
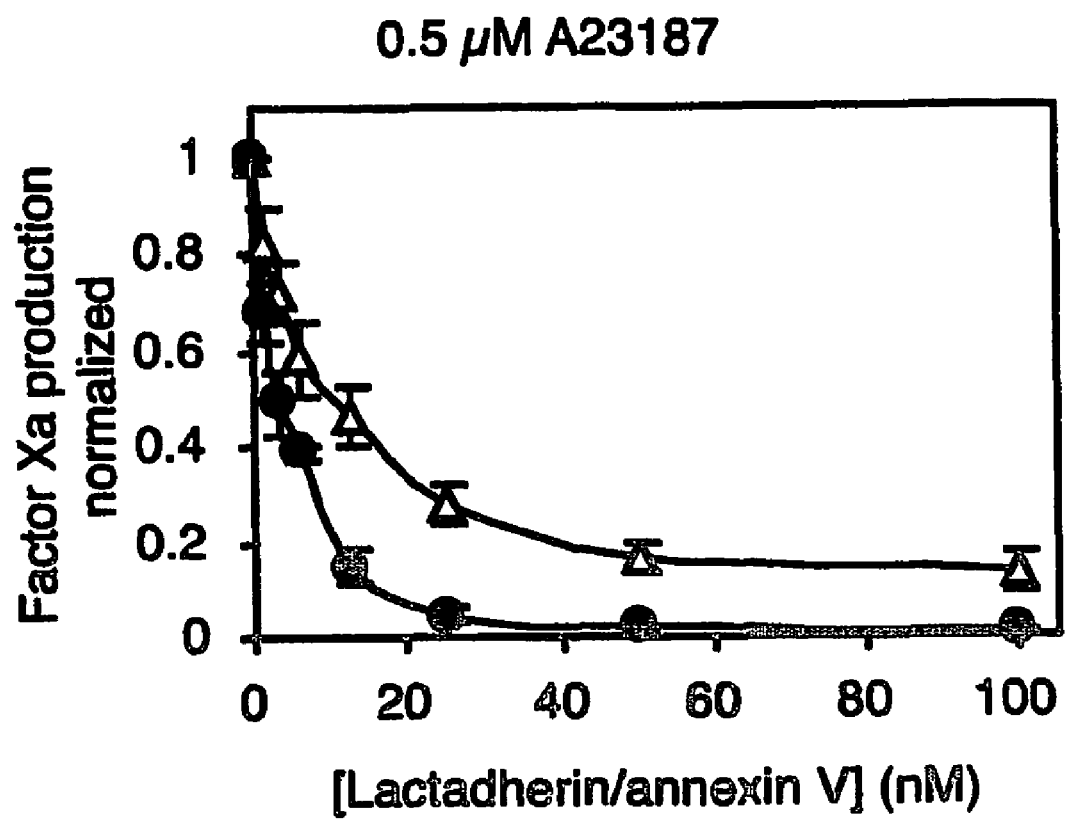

We asked whether lactadherin and annexin V are able to inhibit the procoagulant activity of stimulated platelets attributed to exposed phosphatidylserine. We compared the inhibitory effects of on thrombin formation (FIGS. 10A, 10B) and on factor Xa formation (FIGS. 10C, 10D). Platelets were stimulated either by 0.5 (FIGS. 10A, 10C) or 10 µM A23187 (FIGS. 10B, 10D). We maintained the $Ca^{++}$ concentration at 1.5 mM to simulate plasma. Results showed that lactadherin led to >98% inhibition of thrombin production and >99% inhibition of factor Xa production for both the high and low A23187 concentrations. In contrast, annexin V was less effective, inhibiting 60-80% of platelet prothrombinase activity and factor Xase activity on platelets stimulated at both concentrations of A23187. These results are consistent with the hypothesis that lactadherin detects exposed platelet PS and has the capacity to block the procoagulant activity of the exposed PS.

Figure 11A:
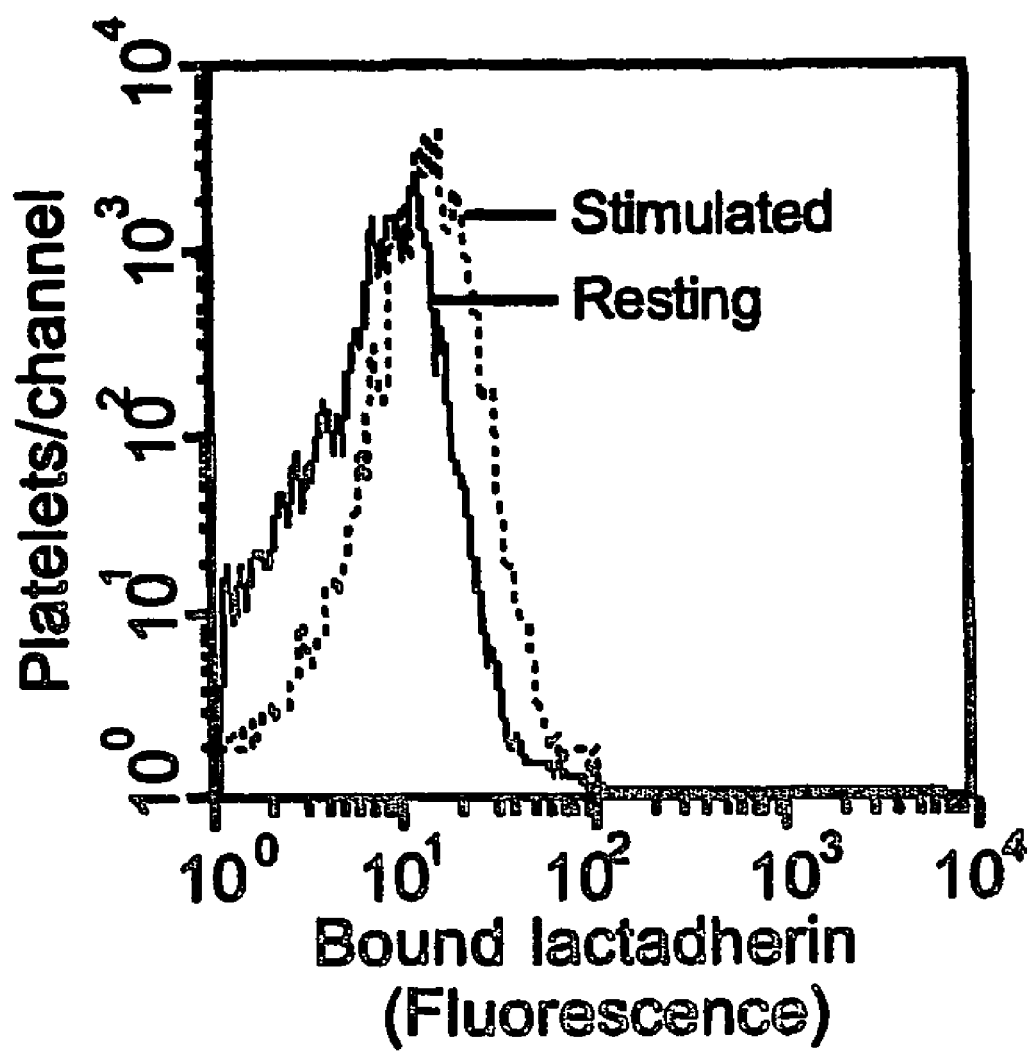
FIG. 11A illustrates expression of lactadherin binding sites on platelets stimulated via the PAR-1 thrombin receptor.
Figure 11B:
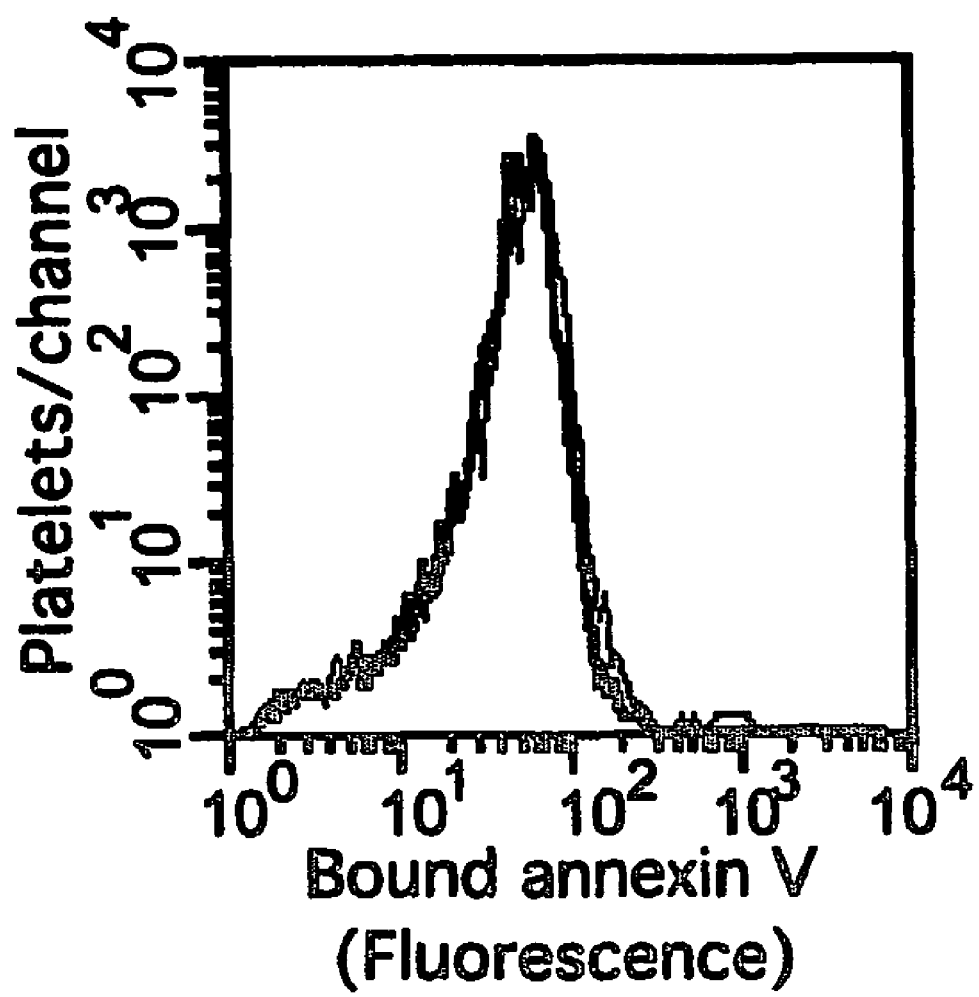
FIG. 11B illustrates absence of expression of annexin V binding sites on platelets stimulated via the PAR-1 receptor.
Figure 11C:
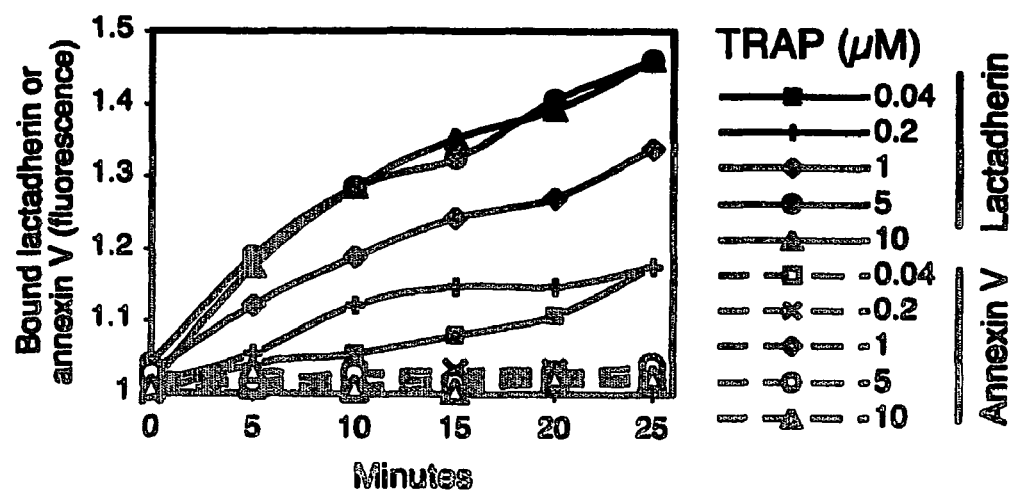
FIG. 11C illustrates kinetic binding of lactadherin (top 5 symbols) or annexin V (lower 5 symbols) for 25 minutes after exposure to various concentrations of the thrombin receptor activation peptide (concentrations depicted adjacent to symbols, R column)

We asked whether thrombin-mediated stimulation of platelets might cause small amounts of PS exposure, analogous to A23187 concentrations of 0.1-0.5 µM (FIGS. 11A-C). Preliminary experiments showed that thrombin caused increased binding of lactadherin (FIG. 11A) but not annexin 5 (FIG. 11B). The quantity of lactadherin that bound to platelets was approximately 25% of the binding that we observed on platelets stimulated with 0.1-0.5 µM A23187. Subsequent experiments, performed with TRAP rather than thrombin, gave equivalent selective enhancement of lactadherin binding. However, usage of TRAP did not require addition of thrombin inhibitors at later stages of the experiment when the objective was to measure prothrombinase-supporting platelet activity. Thus, experiments with TRAP are displayed in FIGS. 11A-C, 12A-C and 13A-B. In order to evaluate the effective stimulatory concentration, platelets were stimulated with 0.04-10 µM TRAP. The results indicated that half maximal lactadherin binding was stimulated by 0.2-1 µM TRAP but that no concentration of TRAP employed increases exposed binding sites for annexin V (FIG. 11C).

Figure 9E:
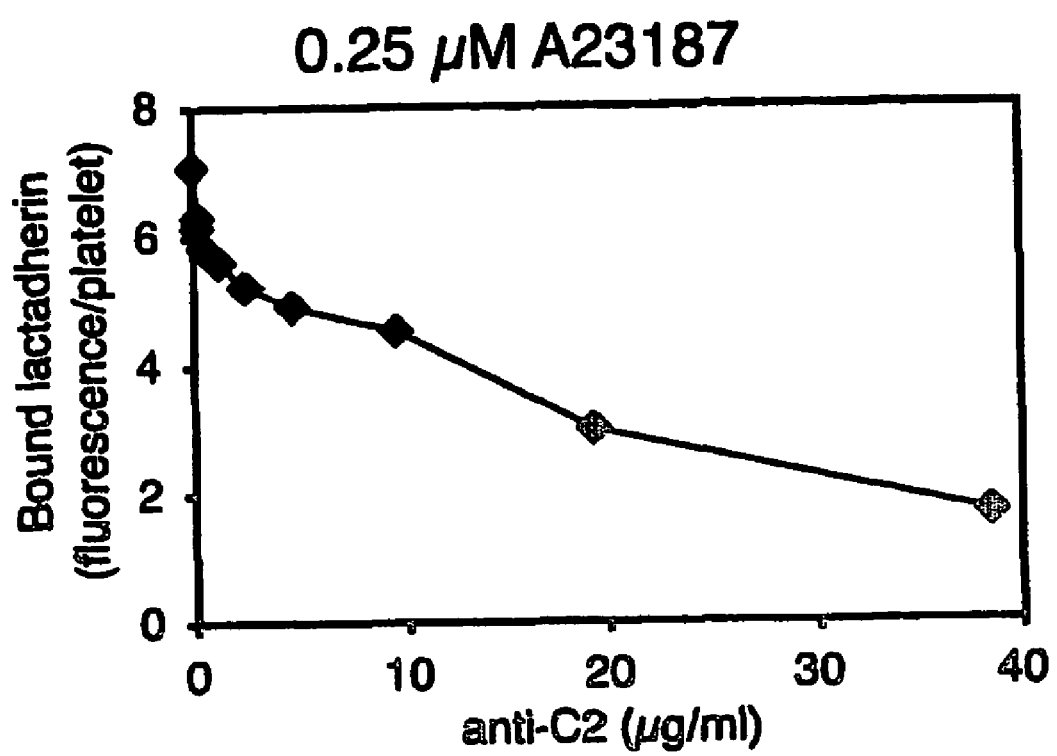
Figure 9F:
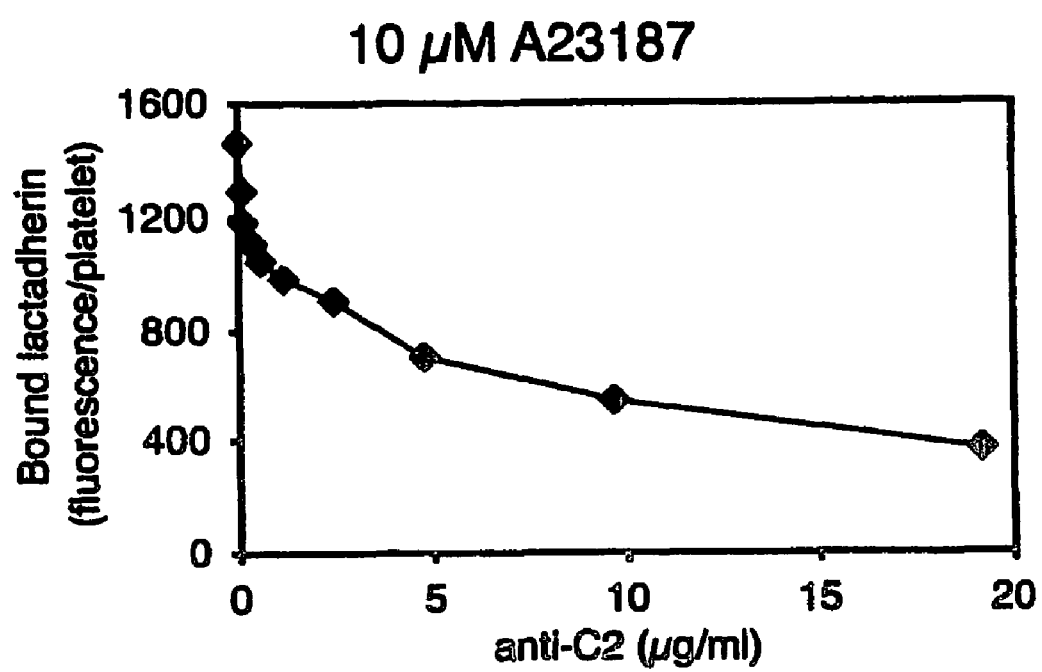

Control experiments were performed to confirm that lactadherin binds to thrombin-stimulated platelets via the PS-binding C2 domain. Binding was not inhibited by calcium chelation or by echistatin, excluding platelet integrins as the binding mediators. Binding to platelets was inhibited by PS-containing phospholipid vesicles, equivalent to inhibition of binding to platelets stimulated with 0.25 µM A23187. Greater than 80% of lactadherin binding was inhibited by the polyclonal antibody against the lactadherin C2 domain (FIG. 9E). These results confirmed that binding of lactadherin to thrombin-stimulated platelets, like binding to A23187-stimulated platelets, is mediated by the PS-binding C2 domain of lactadherin.

Figure 12A:
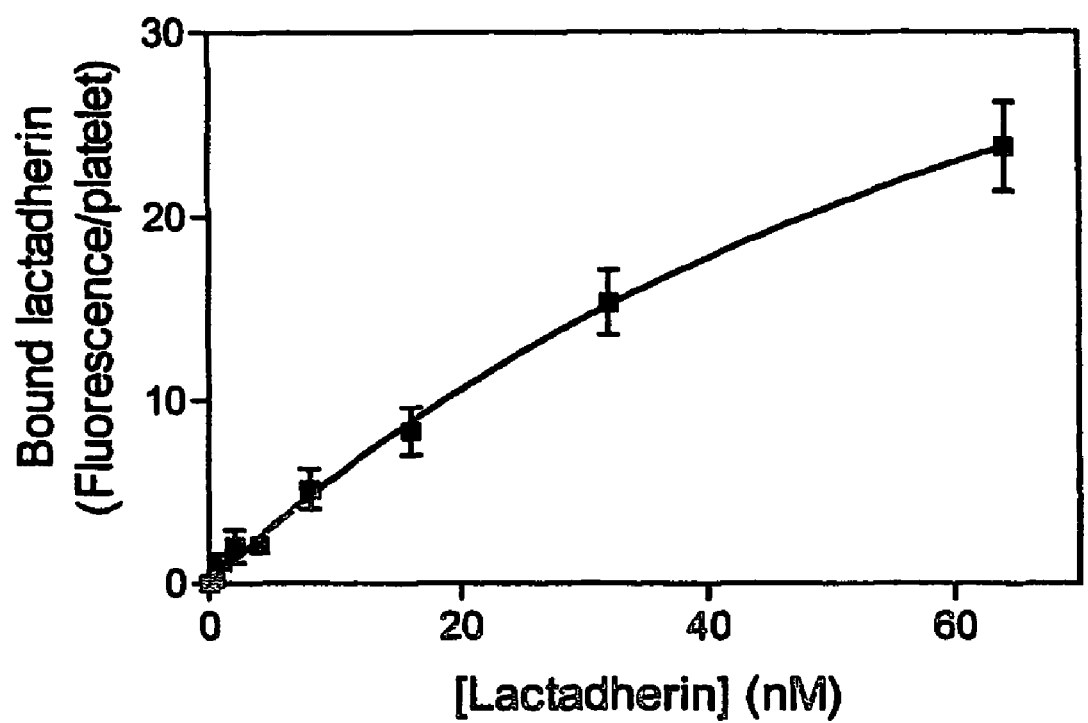
FIGS. 12A-C illustrate equilibrium binding of lactadherin to platelets and exposure of platelet PS. in response to stimulation via the PAR-1 receptor.

To estimate the affinity of lactadherin for thrombin-stimulated platelets, we varied the total lactadherin concentration and measured the quantity bound to platelets (FIG. 12A). Lactadherin bound saturably to these stimulated platelets. The best fit indicated a $K_D$ of 84±28 nM. There were 3200±700 lactadherin binding sites per platelet.

In order to estimate the rate and extent of PS exposure on the platelet plasma membrane we utilized fluorescence-labeled PS (Reference 62). Prior reports indicate that platelets translocate NBD-PS to the inner leaflet of the plasma membrane, like unlabeled PS. When stimulated platelets transfer NBD-PS to the outer leaflet of the plasma membrane it is rapidly exchanged into delipidated albumin that is present in the buffer. Thus, translocation of NBD-PS to the outer plasma membrane causes a net loss in cell fluorescence. NBD-PS was loaded into membranes of resting platelets from donor vesicles prior to platelet purification. The rate and extent of platelet fluorescence loss provide an estimate of the rate and extent of plasma membrane PS exposure.

Figure 12B:
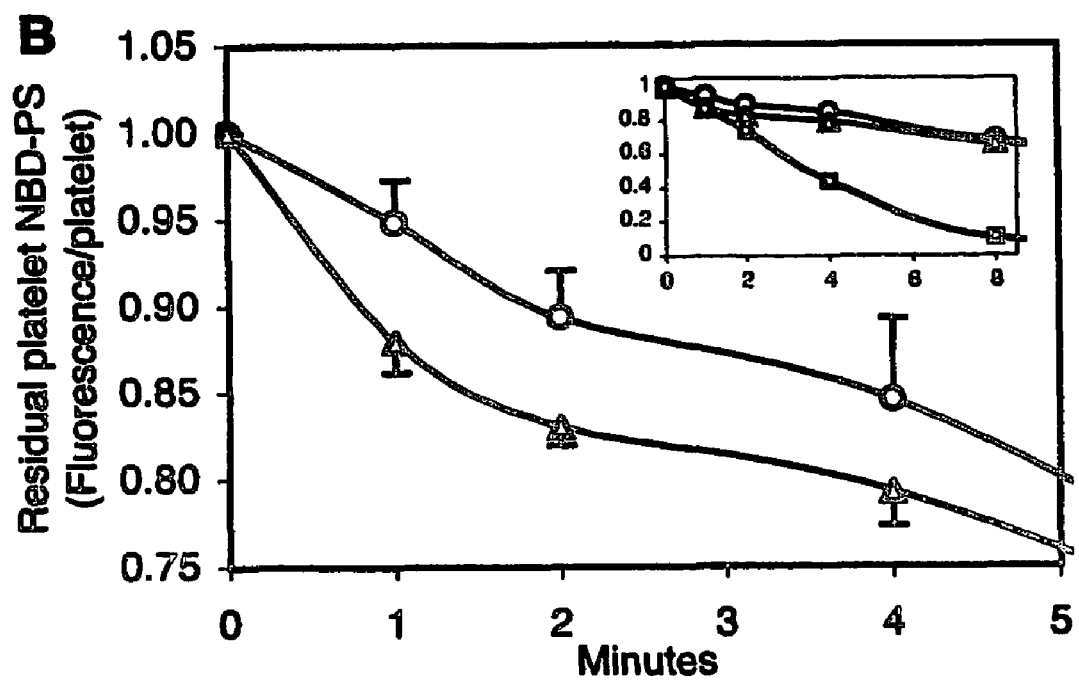

We found that platelet NBD-PS fluorescence decreased after stimulation by TRAP or 10 µM A23187 (FIG. 12B). As illustrated by these data, approximately 25% of platelet fluorescence is lost over 8 min. due to reduction of NBD in the absence of a platelet agonist (Reference 63). During the first minute after addition of TRAP the fluorescence loss was 12±1.8% vs. 5±2.5% for control platelets. Stimulation with 10 µM A23187 led to the same rate of fluorescence loss during the first minute but the rate was maintained so that after 8 min. >90% of NBD fluorescence was lost (FIG. 12B inset). These results confirmed that stimulation by TRAP causes platelets to expose approx. 7% of plasma membrane PS over 1-2 minutes.

Figure 12C:
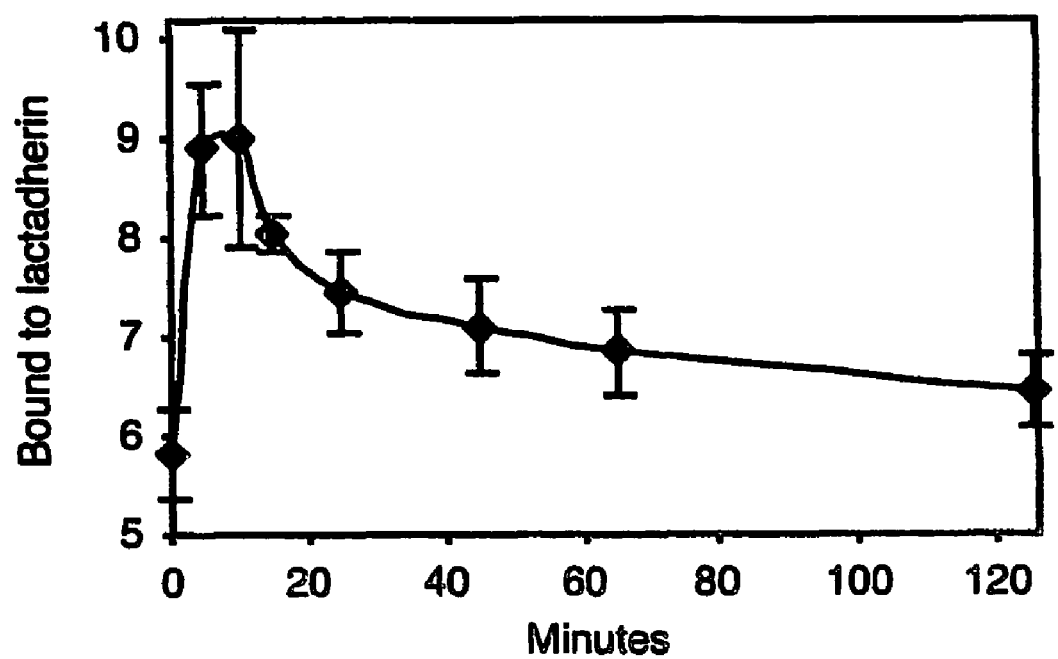

We asked whether TRAP-stimulated PS-exposure is reversible (FIG. 12C). After stimulation by TRAP, platelets were diluted to a concentration at which TRAP is no longer an effective agonist for PS exposure (FIG. 12C). At various times fluorescein-labeled lactadherin was added and platelet fluorescence was recorded by flow cytometry. The results indicated that lactadherin binding sites were maximally exposed by 5-10 min. following stimulation. At later time periods the number of binding sites decreased, with 80% loss by 2 hr after addition of TRAP. These results suggest that TRAP-stimulated expression of lactadherin binding sites begin to decrease within 15 min. after stimulation and are largely removed over the next hour.

Figure 13A:
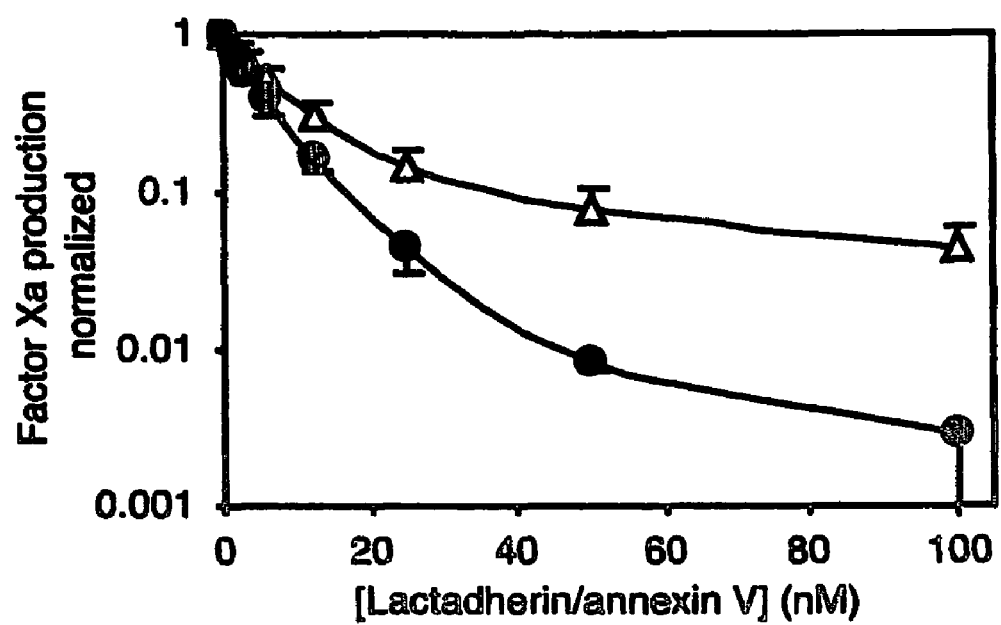
FIG. 13A illustrates inhibition of factor Xa production by lactadherin (●) and annexin V (Δ) bound to platelets stimulated with TRAP.
Figure 13B:
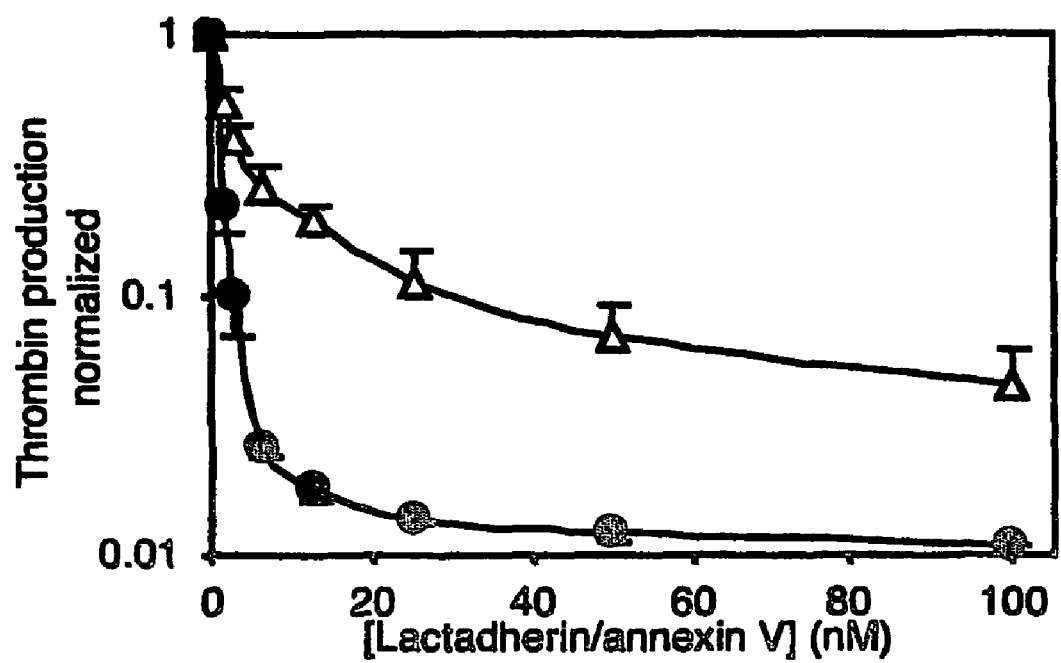
FIG. 13B illustrates inhibition of thrombin production by lactadherin (⊕) and annexin V (Δ) on platelets stimulated by TRAP.

We asked whether the procoagulant activity of TRAP-stimulated platelets is inhibited by lactadherin or by annexin V (FIGS. 13A-B). Annexin V inhibited approximately 90% of activity for both enzyme complexes at a concentration of 50 nM and approached an inhibition plateau with approximately 5-8% of residual activity. Lactadherin was a more effective inhibitor with at least 99% inhibition of the Xase and prothrombinase complexes at 50 nM and inhibition plateaus with <1% residual activity (FIG. 13A). These results indicate that lactadherin is a competitive inhibitor for >99% of procoagulant platelet phosphatidylserine and that annexin V is a less effective inhibitor.

The present invention shows that lactadherin can be used to detect PS exposure on platelet membranes when the PS content is too low to support binding of annexin V. Using lactadherin, we have found that platelets stimulated with 0.1-0.5 µM A23187 or with thrombin expose a small fraction of PS. This low level PS exposure occurs during 1-2 minutes following platelet stimulation and is reversible. Platelets stimulated at this level support the procoagulant activity of the factor Xase and prothrombinase complexes. The capacity of lactadherin to block this platelet procoagulant activity indicates that the limited PS exposure is required for function of the prothrombinase and factor Xase complexes. Thus, our data suggest that transient exposure of small quantities of membrane PS may be a physiologic mechanism through which platelets regulate hemostasis.

Our data indicate that most platelet binding sites for lactadherin are dependent upon interaction of lactadherin with membrane PS. This result was anticipated because the only platelet integrin which lactadherin has the demonstrated capacity to bind, $\alpha_v\beta_3$, is present in low numbers on the platelet membrane (Reference 64). Because binding was not measurably influenced by EDTA or echistatin, we concluded that neither the $\alpha_v\beta_3$ integrin nor other platelet integrins contributed significantly to the observed binding. Further evidence that lactadherin specifically binds exposed PS includes the demonstrated selectivity of lactadherin for phosphatidyl-L-serine, the capacity of an antibody against the PS-binding C2 domain of lactadherin to block binding of lactadherin to platelets, and the capacity of PS-containing phospholipid vesicles to compete with platelets for lactadherin binding.

Prior evidence suggested that thrombin-stimulated, intact platelets have the capacity to express limited quantities of PS. In particular, thrombin-stimulated platelets support both factor Xase and prothrombinase activities (References 34-36). Indeed, PS exposure on thrombin-stimulated platelets has been previously reported (Reference 28). Partial digestion of outer platelet membranes by phospholipases has suggested that 8% of the outer membrane was PS. However, these results were later thought to be partially or entirely explained by the presence of platelet microparticles (Reference 65). The exposure of PS on intact, thrombin-stimulated platelets was called into doubt because annexin V does not demonstrably bind to the membranes (References 29 and 30). Our data resolve the apparent conflict, indicating that intact thrombin-stimulated platelets expose sufficient PS to support binding of lactadherin but not annexin V.

In summary, the results of our studies/experiments confirm that stimulated platelets expose and remove a small fraction of membrane PS, establish a methodology for detection of limited PS exposure on a cell membrane, and provide a basis for testable predictions about PS exposure and its physiologic consequences. This invention is the first to confirm that intact, thrombin-stimulated platelets have the capacity for limited, reversible PS exposure. Lactadherin binding appears to be conveniently adaptable for in vitro studies of PS exposure on platelets as well as nucleated cells. Labeled lactadherin may also be useful as a reagent to image PS exposure on a growing thrombus or a site of inflammation in vivo. The capacity of lactadherin to efficiently inhibit platelet-supported prothrombinase and factor Xase complexes suggest that lactadherin may be useful as a reagent to test hypotheses about the importance of phosphatidylserine for binding of individual blood clotting proteins to cell membranes and for hypotheses about the importance of PS for in vivo thrombosis and hemostasis.

Phospholipases, like lactadherin, bind to Ptd-L-Ser or other negatively charged lipids in highly curved membrane regions to initiate membrane digestion (Reference 66). Thus, it is possible that occupation of curved membrane regions with Ptd-L-Ser by lactadherin may protect milk fat globules from premature digestion by phospholipases or lipases in the epithelial cell, in milk, in the lumen of the GI tract, or in blood.

A recent report demonstrated that in vitro macrophages bind and engulf apoptotic cells by a mechanism in which lactadherin functions as a bridge ligand (Reference 11). Lactadherin binds to phosphatidylserine on apoptotic cells. The macrophages recognize bound lactadherin via the RGD motif and use lactadherin to engulf the apoptotic cells. Our data suggest that in vivo lactadherin might bind to cells, cell membrane vesicles, and possibly lipoproteins that display Ptd-L-Ser and are curved. The immobilized cell, vesicle or particle could then be engulfed by phagocytes. In this way lactadherin may assist in engulfment of fat globules, apocrine secretory vesicles, cellular microparticles. Alternatively, these data suggest that lactadherin might be used as a pharmacologic bridge ligand, targeting drug-laden liposomes to macrophages or other integrin-displaying cells.

In conclusion, the data above indicate that lactadherin binds selectively to Ptd-L-Ser-containing membranes. Like factors VIII and V, it binds preferentially to highly curved membranes.

From the above, one can readily observe and appreciate that lactadherin, a fragment of lactadherin, or a functionally equivalent agent thereof, can be used to detect the presence of a phospholipid, such as phosphatidylserine and/or a phospho-L-serine moiety of phosphatidylserine, in a biological sample, such as a membrane. It can be further used to block or reduce binding of a protein to a binding site, wherein the binding site includes a phospholipid or a lipoprotein, including phosphatidylserine and/or a phospho-L-serine moiety of phosphatidylserine. Other uses of lactadherin, a fragment of lactadherin, or a functionally equivalent agent thereof, include detecting phosphatidylserine-expressing cells and protecting a biological material from the action of an enzyme. Various other uses may be also made by those skilled in the art by following the teachings of the present invention and discovery.

A pharmaceutical composition including lactadherin or a fragment of lactadherin, or a functionally equivalent agent thereof, may be prepared, in a conventional manner. In particular, a pharmaceutical composition made in accordance with the present invention would include lactadherin or a fragment of lactadherin, or a functionally equivalent agent thereof, in an amount sufficient to provide therapeutic and/or prophylactic benefit, in combination with one or more pharmaceutically or physiologically acceptable carriers, diluents or excipients. Compositions of the present invention may be formulated for any appropriate manner for administration, including, for example, oral, nasal, intravenous or intramuscular administration. Appropriate dosages, duration and frequency of administration would be determined by known factors, such as the condition of the patient, the type and severity of the disease and the method of administration.

While this invention has been described as having preferred sequences, ranges, steps, materials, or designs, it is understood that it includes further modifications, variations, uses and/or adaptations thereof following in general the principle of the invention, and including such departures from the present disclosure as those come within the known or customary practice in the art to which the invention pertains, and as may be applied to the central features herein before set forth, and fall within the scope of the invention and of the limits of the appended claims.

All of the references discussed or cited herein are hereby incorporated herein by reference.

REFERENCES

1. Hvarregaard J, Andersen M H, Berglund L, Rasmussen J T, Petersen T E. Characterization of glycoprotein PAS-6/7 from membranes of bovine milk fat globules. Eur. J. Biochem. 1996; 240:628-636.

2. Stubbs J, Lekutis C, Singer K, Bui A, Yuzuki D, Srinivasan U, et al. cDNA cloning of a mouse mammary epithelial cell surface protein reveals the existence of epidermal growth factor-like domains linked to factor VIII-like sequences. Proc. Natl. Acad. Sci., USA 1990; 87:8417-8421.
3. Couto J R, Taylor M R, Godwin S G, Ceriani R L, Peterson J A. Cloning and sequence analysis of human breast epithelial antigen BA46 reveals an RGD cell adhesion sequence presented on an epidermal growth factor-like domain. DNA Cell Biol. 1996; 15 (4):281-6.
4. Andersen M H, Berglund L, Rasmussen J T, Petersen T E. Bovine PAS-6/7 binds $a_vb_5$ integrin and anionic phospholipids through two domains. Biochemistry 1997; 36:5441-5446.
5. Taylor M R, Couto J R, Scallan C D, Ceriani R L, Peterson J A. Lactadherin (formerly BA46), a membrane-associated glycoprotein expressed in human milk and breast carcinomas, promotes Arg-Gly-Asp (RGD)-dependent cell adhesion. DNA Cell Biol. 1997; 16 (7):861-9.
6. Andersen M H, Graversen H, Fedosov S N, Petersen T E, Rasmussen J T. Functional analyses of two cellular binding domains of bovine lactadherin. Biochemistry 2000; 39 (20):6200-6.
7. Butler J E, Pringnitz D J, Martens C L, Crouch N. Bovine-associated mucoprotein: I. Distribution among adult and fetal bovine tissues and body fluids. Differentiation 1980; 17 (1):31-40.
8. Peterson J A, Couto J R, Taylor M R, Ceriani R L. Selection of tumor-specific epitopes on target antigens for radioimmunotherapy of breast cancer. Cancer Res. 1995; 55 (23 Suppl):5847s-5851s.
9. Haggqvist B, Naslund J, Sletten K, Westermark G T, Mucchiano G, Tjernberg L O, et al. Medin: an integral fragment of aortic smooth muscle cell-produced lactadherin forms the most common human amyloid. Proc. Natl. Acad. Sci. U.S.A. 1999; 96 (15):8669-74.
10. Ensslin M, Calvete J J, Thole H H, Sierralta W D, Adermann K, Sanz L, et al. Identification by affinity chromatography of boar sperm membrane-associated proteins bound to immobilized porcine zona pellucida. Mapping of the phosphorylethanolamine-binding region of spermadhesin AWN. Biol. Chem. Hoppe. Seyler 1995; 376 (12): 733-8.
11. Hanayama R, Tanaka M, Miwa K, Shinohara A, Iwamatsu A, Nagata S. Identification of a factor that links apoptotic cells to phagocytes. Nature 2002; 417 (6885): 182-7.
12. Shi J, Gilbert G E. Lactadherin inhibits enzyme complexes of blood coagulation by competing for phospholipid binding sites. Blood 2003; 101 (7):2628-36.
13. Arai M, Scandella D, Hoyer L. Molecular basis of factor VIII inhibition by human antibodies. Antibodies that bind to the factor VIII light chain prevent the interaction of factor VIII with phospholipid. J. Clin. Invest. 1989; 83:1978-1984.
14. Foster P A, Fulcher C A, Houghten R A, Zimmerman T S. Synthetic factor VIII peptides with amino acid sequences contained within the C2 domain of factor VIII inhibit factor VIII binding to phosphatidylserine. Blood 1990; 75:1999-2004.
15. Ortel T, Devore-Carter D, Quinn-Allen M, Kane W. Deletion analysis of recombinant human factor V: Evidence for a phosphatidylserine binding site in the second C-type domain. J. Biol. Chem. 1992; 267:4189-4198.
16. Gilbert G E, Furie B C, Furie B. Binding of human factor VIII to phospholipid vesicles. J. Biol. Chem. 1990; 265: 815-822.
17. Gilbert G E, Drinkwater D, Barter S, Clouse S B. Specificity of phosphatidylserine-containing membrane binding sites for factor VIII: Studies with model membranes supported by glass microspheres (Liposheres). J. Biol. Chem. 1992; 267:15861-15868.
18. Gilbert G E, Drinkwater D. Specific membrane binding of factor VIII is mediated by O-phospho-L-serine, a moiety of phosphatidylserine. Biochemistry 1993; 32:9577-9585.
19. Comfurius P, Smeets E F, Willems G M, Bevers E M, Zwaal R F A. Assembly of the prothrombinase complex on lipid vesicles depends on the stereochemical configuration of the polar headgroup of phosphatidylserine. Biochemistry 1994; 33 (34):10319-10324.
20. Bardelle C, Furie B, Furie B C, Gilbert G E. Kinetic Studies of Factor VIII Binding to Phospholipid Membranes Indicate a Complex Binding Process. J. Biol. Chem. 1993; 268:8815-24.
21. Gilbert G E, Arena M. Phosphatidylethanolamine induces high affinity binding sites for factor VIII on membranes containing phosphatidyl-L-serine. J. Biol. Chem. 1995; 270:18500-18505.
22. Gilbert G E, Arena A A. Unsaturated phospholipid acyl chains are required to constitute membrane binding sites for factor VIII. Biochemistry 1998; 37 (39): 13526-35.
23. Pratt K P, Shen B W, Takeshima K, Davie E W, Fujikawa K, Stoddard B L. Structure of the C2 domain of human factor VIII at 1.5 angstrom resolution. Nature. 1999; 402 (6760):439-442.
24. Macedo-Ribeiro S, Bode W, Huber R, Quinn-Allen M A, Kim S W, Ortel T L, et al. Crystal structures of the membrane-binding C2 domain of human coagulation factor V. Nature. 1999; 402 (6760):434-439.
25. Kim S W, Quinn-Allen M A, Camp J T, Macedo-Ribeiro S, Fuentes-Prior P, Bode W, et al. Identification of functionally important amino acid residues within the C2-domain of human factor V using alanine-scanning mutagenesis. Biochemistry 2000; 39 (8):1951-8.
26. Gilbert G E, Kaufman R J, Arena M, Miao H. Pipe S W. Four hydrophobic amino acids of the factor VIII C2 domain are constituents of both the membrane-binding and von Willebrand factor-binding motifs. J Biol Chem 2002; 277 (8):6374-81.
27. Peterson J A, Patton S, Hamosh M. Glycoproteins of the human milk fat globule in the protection of the breast-fed infant against infections. Biol. Neonate 1998; 74 (2): 143-62.
28. Bevers E, Comfurius P, Zwaal R. Changes in membrane phospholipid distribution during platelet activation. Biochim. Biophys. Acta 1983; 736:57-66.
29. Dachary-Prigent J, Freyssinet J M, Pasquet J M, Carron J C, Nurden A T. Annexin V as a probe of aminophospholipid exposure and platelet membrane vesiculation: a flow cytometry study showing a role for free sulfhydryl groups. Blood 1993; 81 (10):2554-65.
30. Alberio L, Safa O, Clemetson K J, Esmon C T, Dale G L. Surface expression and functional characterization of alpha-granule factor V in human platelets: effects of ionophore A23187, thrombin, collagen, and convulxin. Blood 2000; 95 (5): 1694-702.
31. Zwaal R, Comfurius P, van Deenen L. Membrane asymmetry and blood coagulation. Nature 1977; 268:358-360.
32. Bevers E, Comfurius P, Van Rijn J, Hemker H, Zwaal R. Generation of Prothrombin-Converting Activity and the Exposure of Phosphatidylserine at the Outer Surface of Platelets. Eur. J. Biochem. 1982; 122:429-436.
33. Seigneuret M, Devaux P F. ATP-dependent asymmetric distribution of spin-labeled phospholipids in the erythro- 34. Tracy P, Peterson J, Nesheim M, McDuffie F, Mann K. Interaction of coagulation factor V and factor Va with platelets. J. Biol. Chem. 1979; 254:10345.

35. Swords N A, Tracy P B, Mann K G. Intact Platelet Membranes, Not Platelet-Released Microvesicles, Support the Procoagulant Activity of Adherent Platelets. Arterioscier. Thromb. 1993; 13(11):1613-1622.

36. Ahmad S S, Rawala-Sheikh R, Ashby B, Walsh P N. Platelet receptor-mediated factor X activation by factor IXa: High-affinity factor IXa receptors induced by factor VIII are deficient on platelets in Scott syndrome. J. Clin. Invest. 1989; 84:824-828.

37. Gilbert G E, Sims P J, Wiedmer T. Furie B, Furie B C, Shattil S J. Platelet-derived microparticles express high affinity receptors for factor VIII. J. Biol. Chem. 1991; 266:17261-68.

38. Comfurius P, Bevers E M, Zwaal R F A. Enzymatic synthesis of phosphatidylserine on small scale by use of a one-phase system. J. Lipid Res. 1990; 31:1719-1721.

39. Hope M J, Bally M B, Webb G, Cullis P R. Production of large unilamellar vesicles by a rapid extrusion procedure. Characterization of size distribution, trapped volume and ability to maintain a membrane potential. Biochim. Biophys. Acta 1985; 812:55-65.

40. Chen P, Toribara T, Warner H. Microdetermination of phosphorus. Anal. Chem. 1956; 28:1756-1758.

41. Huang C, Mason J. Geometric packing constraints in egg phosphatidylcholine vesicles. Proc. Natl. Acad. Sci., USA 1978; 75:308-310.

42. Bangham A D, Standish M M, Watkins J C. Diffusion of univalent ions across the lamellae of swollen phospholipids. J. Mol. Biol. 1965; 13:238-252.

43. Pusey M, Mayer L, Wei G, Bloomfield V, Nelsestuen G. Kinetic and Hydrodynamic Analysis of Blood Clotting Factor V-Membrane Binding. Biochemistry 1982; 21:5262-5269.

44. Abbott A, Nelsestuen G. Association of a Protein with Membrane Vesicles at the Collisional Limit: Studies with Blood Coagulation Factor Va Light Chain Also Suggest Major Differences between Small and Large Unilamellar Vesicles. Biochemistry 1987; 26:7994-8003.

45. Bloom J W. The interaction of rDNA factor VIII, factor VIIIdes-797-1562 and factor VIIIdes-797-1562 derived peptides with phospholipid. Throm. Res. 1987; 48:439-448.

46. Epand R M, Stevenson C, Bruins R, Schram V, Glaser M. The chirality of phosphatidylserine and the activation of protein kinase C. Biochemistry 1998; 37 (35): 12068-73.

47. Berden J A, Barker R W, Radda G K. NMR studies on phospholipid bilayers. Some factors affecting lipid distribution. Biochim. Biophys. Acta 1975; 375 (2):186-208.

48. Barsukov L I, Victorov A V, Vasilenko I A, Evstigneeva R P, Bergelson L D. Investigation of the inside-outside distribution, intermembrane exchange and transbilayer movement of phospholipids in sonicated vesicles by shift reagent NMR. Biochim. Biophys. Acta 1980; 598 (1):153-68.

49. Litman B J. Determination of molecular asymmetry in the phosphatidylethanolamine surface distribution in mixed phospholipid vesicles. Biochemistry 1974; 13 (14):2844-8.

50. Koynova R D, Tenchov B G. Effect of ion concentration on phosphatidylethanolamine distribution in mixed vesicles. Biochim. Biophys. Acta 1983; 727 (2):351-6.

51. Lentz B R, Litman B J. Effect of head group on phospholipid mixing in small, unilamellar vesicles: mixtures of dimyristoylphosphatidylcholine and dimyristoylphosphatidylethanolamine. Biochemistry 1978; 17 (25):5537-43.

52. Nordlund J R, Schmidt C F, Dicken S N, Thompson T E. Transbilayer distribution of phosphatidylethanolamine in large and small unilamellar vesicles. Biochemistry 1981; 20 (11):3237-41.

53. Tait J F, Gibson D. Phospholipid binding of annexin V: effects of calcium and membrane phosphatidylserine content. Arch. Biochem. Biophys. 1992; 298 (1): 187-91.

54. Andree H, Reutelingsperger C, Hauptmann R, Hemker H, Hermens W, Willems G. Binding of vascular anticoagulant a (VACa) to planar phospholipid bilayers. J. Biol. Chem. 1990; 265:4923-4928.

55. Andree H A, Stuart M C, Hermens W T, Reutelingsperger C P, Hemker H C, Frederik P M, et al. Clustering of lipid-bound annexin V may explain its anticoagulant effect. J. Biol. Chem. 1992; 267 (25):17907-12.

56. Swairjo M A, Concha N O, Kaetzel M A, Dedman J R, Seaton B A. Ca2+-bridging mechanism and phospholipid head group recognition in the membrane-binding protein annexin V. Nat. Struct. Biol. 1995; 2:968-974.

57. Pigault C, Follenius-Wund A, Schmutz M, Freyssinet J M, Brisson A. Formation of two-dimensional arrays of annexin V on phosphatidylserine-containing liposomes. J. Mol. Biol. 1994; 236 (1):199-208.

58. Koopman G, Reutelingsperger C P, Kuijten G A, Keehnen R M, Pals S T, van Oers M H. Annexin V for flow cytometric detection of phosphatidylserine expression on B cells undergoing apoptosis. Blood 1994; 84 (5):1415-20.

59. Connor J, Bucana C, Fidler I J, Schroit A J. Differentiation-dependent expression of phosphatidylserine in mammalian plasma membranes: Quantitative assessment of outer-leaflet lipid by prothrombinase complex formation. Proc. Natl. Acad. Sci. USA 1989; 86:3184-3188.

60. Poste G, Papahadjopoulos D. Lipid vesicles as carriers for introducing materials into cultured cells: influence of vesicle lipid composition on mechanism(s) of vesicle incorporation into cells. Proc. Natl. Acad. Sci. U.S.A. 1976; 73 (5): 1603-7.

61. Batzri S, Korn E D. Interaction of phospholipid vesicles with cells. Endocytosis and fusion as alternate mechanisms for the uptake of lipid-soluble and water-soluble molecules. J. Cell Biol. 1975; 66 (3):621-34.

62. Chang C P, Zhao J, Wiedmer T, Sims P J. Contribution of platelet microparticle formation and granule secretion to the transbilayer migration of phosphatidylserine. J. Biol. Chem. 1993; 268:7171-7178.

63. McIntyre J C, Sleight R G. Fluorescence Assay for Phospholipid Membrane Asymmetry. Biochemistry 1991; 30:11819-11827.

64. Lawler J, Hynes R O. An integrin receptor on normal and thrombasthenic platelets that binds thrombospondin. Blood 1989; 74 (6):2022-7.

65. Bevers E, Wiedmer T, Comfurius P, Shattil S, Weiss H, Zwaal R, et al. Defective Ca2+-Induced Microvesiculation and Deficient Expression of Procoagulant Activity in Erythrocytes From a Patient With a Bleeding Disorder: A Study of the Red Blood Cells of Scott Syndrome. Blood 1992; 79:380-388.

66. Jain M K, Rogers J, Marecek J F, Ramirez F, Eibl H. Effect of the structure of phospholipid on the kinetics of intra-vesicle scooting of phospholipase A2. Biochim. Biophys. Acta 1986; 860 (3):462-74.

What is claimed is:

1. A method of detecting the presence of a phospholipid in a biological material, comprising the steps of:
   a) providing a biological material;
   b) contacting the biological material with at least one binding agent selected from the group consisting of lactadherin, a fragment of lactadherin, a functional equivalent of lactadherin, and a functional equivalent of a fragment of lactadherin;
   c) binding the biological material and the binding agent; and
   d) detecting the presence of any phospholipid bound to the binding agent or the binding agent bound to the biological material.

2. The method of claim 1, wherein:
   the phospholipid comprises phosphatidylserine.

3. The method of claim 1, wherein:
   the phospholipid comprises a phospho-L-serine moiety of phosphatidylserine.

4. The method of claim 2, wherein:
   the biological material comprises a cell, a cell membrane, a cell appendage, a cell fragment, a lipoprotein, or a cellular particle.

5. The method of claim 4, wherein:
   any binding in step c) is independent of any $Ca^{++}$ or phosphatidylethanolamine.

6. The method of claim 4, wherein:
   any binding in step c) is increased with increasing of cell membrane curvature.

7. The method of claim 2, wherein:
   any binding in step c) increases proportionally to the content of phosphatidylserine in a range of about 0-2%.

8. The method of claim 4, wherein:
   the cell membrane comprises a curved region.

* * * * *